US010526592B2

(12) United States Patent
Kim et al.

(10) Patent No.: US 10,526,592 B2
(45) Date of Patent: Jan. 7, 2020

(54) BETA-GALACTOSIDASE VARIANT HAVING HIGH TRANSGLYCOSYLATION ACTIVITY, AND USE THEREOF

(71) Applicant: GENOFOCUS CO., LTD., Daejeon (KR)

(72) Inventors: Su Jin Kim, hungcheongnam-do (KR); Young-Jae Eu, Daejeon (KR); Taek Ho Yang, Daejeon (KR); Jae Gu Pan, Sejong-si (KR); Eui Joong Kim, Daejeon (KR)

(73) Assignee: GENOFOCUS CO., LTD., Daejeon (KR)

( * ) Notice: Subject to any disclaimer, the term of this patent is extended or adjusted under 35 U.S.C. 154(b) by 0 days.

(21) Appl. No.: 15/574,559

(22) PCT Filed: May 19, 2016

(86) PCT No.: PCT/KR2016/005335
§ 371 (c)(1),
(2) Date: Nov. 16, 2017

(87) PCT Pub. No.: WO2016/190613
PCT Pub. Date: Dec. 1, 2016

(65) Prior Publication Data
US 2018/0155699 A1 Jun. 7, 2018

(30) Foreign Application Priority Data

May 28, 2015 (KR) .......................... 10-2015-0074862

(51) Int. Cl.
| | |
|---|---|
| C12N 9/24 | (2006.01) |
| C12P 19/04 | (2006.01) |
| C12N 15/75 | (2006.01) |
| C12N 15/80 | (2006.01) |
| C12N 15/81 | (2006.01) |
| C12P 19/14 | (2006.01) |

(52) U.S. Cl.
CPC ........... *C12N 9/2402* (2013.01); *C12N 15/75* (2013.01); *C12N 15/80* (2013.01); *C12N 15/81* (2013.01); *C12P 19/04* (2013.01); *C12P 19/14* (2013.01); *C12Y 302/01023* (2013.01)

(58) Field of Classification Search
CPC .................................................. C12N 9/2402
See application file for complete search history.

(56) References Cited

U.S. PATENT DOCUMENTS

2012/0135468 A1 5/2012 Katase et al.

FOREIGN PATENT DOCUMENTS

| | | |
|---|---|---|
| EP | 0307247 B1 | 3/1989 |
| KR | 10-2011-0102862 A | 9/2011 |
| KR | 10-1121161 B1 | 3/2012 |
| WO | 9108291 A2 | 6/1991 |
| WO | 2015046408 A1 | 4/2015 |

OTHER PUBLICATIONS

Ishikawa, K., et al., "Crystal Structure of Beta-Galactosidase from Bacillus Circulans ATCC 31382 (BgaD) and the Construction of the Thermophilic Mutants", "The FEBS Journal", 2015, pp. 2540-2552, vol. 282, No. 13.
Juers, D. H., et al., "A Structural View of the Action of *Escherichia coli* (lacZ) b-Galactosidase", "Biochemistry", Nov. 15, 2001, pp. 14781-14794, vol. 40.
Macfarlane, G. T., et al., "Bacterial metabolism and health-related effects of galacto-oligosaccharides and other prebiotics", "Journal of Applied Microbiology", 2008, pp. 305-344, vol. 104.
Mandecki, W., et a l., "Position of the lacZX90 Mutation and Hybridization Between Complete and Incomplete b-Galactosidase", "Journal of Bacteriology", Aug. 1981, pp. 694-697, vol. 147, No. 2.
Mozaffar, Z., et al., "Purification and Properties of b-Galactosidases from Bacillus circulans", "Agricultural and Biological Chemistry", 1984, pp. 3053-3061, vol. 48, No. 12.
Silk, D. B. A., et al., "Clinical trial: the effects of a trans-galactooligosaccharide prebiotic on faecal microbiota and symptoms in irritable bowel syndrome", "Alimentary Pharmacology & Therapeutics", 2009, pp. 508-518, vol. 29.
Song, J., et al., "Cloning and Expression of a b-Galactosidase Gene of Bacillus ciruclans", "Bioscience, Biotechnology, and Biochemistry", Jun. 13, 2011, pp. 1194-1197, vol. 75, No. 6.
Song, J., et al., "Causes of the Production of Multiple Forms of b-Galactosidase by Bacillus circulans", "Bioscience, Biotechnology, and Biochemistry", Feb. 7, 2011, pp. 268-278, vol. 75, No. 2.
Vetere, A., et al., "Separation and characterization of three b-galactosidases from Bacilus circulans", "Biochimica et Biophysica Acta", 1998, pp. 223-231, vol. 1380.
Note: For the non-patent literature citations that no month of publication is indicated, the year of publication is more than 1 year prior to the effective filing date of the present application.

*Primary Examiner* — Suzanne M Noakes
(74) *Attorney, Agent, or Firm* — Hultquist, PLLC; Steven J. Hultquist

(57) ABSTRACT

The present invention relates to a beta-galactosidase mutant having high transglycosylation activity and containing a C-terminal deletion, and the use thereof and more. More specifically, the present invention relates to a beta-galactosidase mutant having a C-terminal deletion, a gene encoding the same, a recombinant vector containing the gene, a recombinant microorganism transformed with the gene or the recombinant vector, and a method for producing the beta-galactosidase mutant using the recombinant microorganism. Using the high transglycosylation activity of the beta-galactosidase mutant containing the C-terminal deletion according to the present invention, galactooligosaccharide can be efficiently produced in large amounts.

7 Claims, 6 Drawing Sheets

Specification includes a Sequence Listing.

SEQUENCE LISTING

<160> NUMBER OF SEQ ID NOS: 27

<210> SEQ ID NO 1
<211> LENGTH: 38
<212> TYPE: DNA

```
<213> ORGANISM: Artificial Sequence
<220> FEATURE:
<223> OTHER INFORMATION: D92-BgaII-F

<400> SEQUENCE: 1
aggaagaaaa ggatccatga gacgaattaa ttttaatg                            38

<210> SEQ ID NO 2
<211> LENGTH: 37
<212> TYPE: DNA
<213> ORGANISM: Artificial Sequence
<220> FEATURE:
<223> OTHER INFORMATION: BgaII-D92-R

<400> SEQUENCE: 2
gcgaccggcg ctcagctgtc attctgtaaa acgaatg                             37

<210> SEQ ID NO 3
<211> LENGTH: 1396
<212> TYPE: PRT
<213> ORGANISM: Artificial Sequence
<220> FEATURE:
<223> OTHER INFORMATION: BgaII

<400> SEQUENCE: 3
```

| Met | Arg | Arg | Ile | Asn | Phe | Asn | Asp | Asn | Trp | Arg | Phe | Gln | Arg | Glu | Ile |
|---|---|---|---|---|---|---|---|---|---|---|---|---|---|---|---|
| 1 | | | | 5 | | | | | 10 | | | | | 15 | |

| Ser | Thr | Ser | Leu | Arg | Glu | Ala | Gln | Lys | Pro | Ser | Phe | Asn | Asp | His | Ser |
|---|---|---|---|---|---|---|---|---|---|---|---|---|---|---|---|
| | | | 20 | | | | | 25 | | | | | 30 | | |

| Trp | Arg | Gln | Leu | Ser | Leu | Pro | His | Asp | Trp | Ser | Ile | Glu | Leu | Asp | Phe |
| | | | 35 | | | | | 40 | | | | | 45 | | |

| Asn | Lys | Asp | Ser | Leu | Ala | Thr | His | Glu | Gly | Gly | Tyr | Leu | Asp | Gly | Gly |
| 50 | | | | | 55 | | | | | 60 | | | | | |

| Val | Gly | Trp | Tyr | Arg | Lys | Thr | Phe | Thr | Val | Pro | Ser | Ala | Met | Glu | Gly |
| 65 | | | | 70 | | | | | 75 | | | | | 80 | |

| Lys | Arg | Ile | Ser | Leu | Asp | Phe | Asp | Gly | Val | Tyr | Met | Asn | Ser | Thr | Thr |
| | | | | 85 | | | | | 90 | | | | | 95 | |

| Tyr | Leu | Asn | Gly | Glu | Glu | Leu | Gly | Thr | Tyr | Pro | Phe | Gly | Tyr | Asn | Ala |
| | | | 100 | | | | | 105 | | | | | 110 | | |

| Phe | Ser | Tyr | Asp | Ile | Thr | Asp | Lys | Leu | Phe | Met | Asp | Gly | Arg | Glu | Asn |
| | | | 115 | | | | | 120 | | | | | 125 | | |

| Val | Leu | Ala | Val | Lys | Val | Asp | Asn | Thr | Gln | Pro | Ser | Ser | Arg | Trp | Tyr |
| | 130 | | | | | 135 | | | | | 140 | | | | |

| Ser | Gly | Ser | Gly | Ile | Tyr | Arg | Asn | Val | Tyr | Leu | Thr | Val | Thr | Asn | Pro |
| 145 | | | | | 150 | | | | | 155 | | | | | 160 |

| Val | His | Val | Ala | Arg | Tyr | Gly | Thr | Phe | Val | Thr | Thr | Pro | Asp | Leu | Glu |
| | | | | 165 | | | | | 170 | | | | | 175 | |

| Ser | Ala | Tyr | Ala | Ala | Arg | Lys | Ala | Glu | Val | Asn | Ile | Lys | Thr | Lys | Ile |
| | | | 180 | | | | | 185 | | | | | 190 | | |

| Asn | Asn | Asp | Ser | Asp | Ala | Ala | Val | Gln | Val | Lys | Val | Ser | Thr | Ile |
| | | | 195 | | | | | 200 | | | | | 205 | |

| Tyr | Asp | Thr | Asp | Gly | Lys | Glu | Val | Ala | Ser | Val | Val | Ser | Gln | Glu | Lys |
| | 210 | | | | | 215 | | | | | 220 | | | | |

| Thr | Ala | Ala | Ala | Gly | Thr | Thr | Ala | His | Phe | Glu | Asp | Asn | Thr | Val | Ile |
| 225 | | | | | 230 | | | | | 235 | | | | | 240 |

| Glu | Asn | Pro | Glu | Leu | Trp | Ser | Leu | Asp | Asn | Pro | Tyr | Arg | Tyr | Lys | Leu |
| | | | | 245 | | | | | 250 | | | | | 255 | |

| Val | Thr | Asp | Val | Leu | Ile | Gly | Gly | Glu | Thr | Val | Asp | Thr | Tyr | Glu | Thr |

-continued

```
                260                 265                 270
Arg Phe Gly Ala Arg Phe Phe Lys Phe Asp Ala Asn Glu Gly Phe Ser
            275                 280                 285

Leu Asn Gly Lys Pro Met Lys Leu Tyr Gly Val Ser Met His His Asp
        290                 295                 300

Leu Gly Ala Leu Gly Ala Ala Thr Asn Ala Arg Ala Val Glu Arg Gln
305                 310                 315                 320

Leu Gln Ile Met Lys Asp Met Gly Val Asn Ala Ile Arg Gly Thr His
                325                 330                 335

Asn Pro Val Ser Pro Glu Phe Leu Glu Ala Val Asn Asn Leu Gly Leu
            340                 345                 350

Leu Leu Ile Glu Glu Ala Phe Asp Cys Trp Ser Gln Ser Lys Lys Thr
        355                 360                 365

Tyr Asp Tyr Gly Arg Phe Phe Thr Arg Trp Ala Glu His Asp Val Lys
    370                 375                 380

Glu Met Val Asp Arg Gly Lys Asn Glu Pro Ser Ile Ile Met Trp Ser
385                 390                 395                 400

Ile Gly Asn Glu Ile Tyr Asp Thr Thr Ser Pro Ser Gly Val Glu Thr
                405                 410                 415

Ala Arg Asn Leu Val Arg Trp Ile Lys Glu Ile Asp Thr Thr Arg Pro
            420                 425                 430

Thr Thr Ile Gly Glu Asp Lys Thr Arg Gly Asp Lys Val Asn Val Thr
        435                 440                 445

Pro Ile Asp Pro Asn Ile Leu Glu Ile Phe His Thr Val Asp Val Val
    450                 455                 460

Gly Leu Asn Tyr Ser Glu Asn Asn Tyr Val Gly Tyr His Glu Gln His
465                 470                 475                 480

Pro Asn Trp Lys Leu Tyr Gly Ser Glu Thr Ser Ser Ala Thr Arg Ser
                485                 490                 495

Arg Gly Val Tyr Thr His Pro Tyr Glu Tyr Asn Leu Gly Thr Lys Tyr
            500                 505                 510

Asp Asp Leu Gln Gln Ser Ser Tyr Asp Asn Asp Tyr Val Pro Trp Gly
        515                 520                 525

Arg Thr Ala Glu Asp Ala Trp Lys Ser Asp Arg Asp Leu Lys His Phe
    530                 535                 540

Ala Gly Gln Phe Ile Trp Thr Gly Phe Asp Tyr Ile Gly Glu Pro Thr
545                 550                 555                 560

Pro Tyr Tyr Asp Ser Tyr Pro Ala Lys Ser Ser Tyr Phe Gly Ala Val
                565                 570                 575

Asp Thr Ala Gly Phe Pro Lys Asp Ile Phe Tyr Tyr Gln Ser Gln
            580                 585                 590

Trp Lys Lys Glu Pro Met Val His Leu Leu Pro His Trp Asn Trp Thr
        595                 600                 605

Glu Gly Glu Pro Val Arg Val Leu Ala Tyr Thr Asn Ala His Gln Val
    610                 615                 620

Glu Leu Phe Leu Asn Gly Lys Ser Leu Gly Val Arg Gly Tyr Glu Asn
625                 630                 635                 640

Lys Lys Thr Ser Trp Gly Ala Pro Tyr Lys Glu Thr Lys Asp Gly Lys
                645                 650                 655

Thr Tyr Leu Glu Trp Ala Val Pro Phe Lys Ala Gly Thr Leu Glu Ala
            660                 665                 670

Val Ala Met Asp Glu Asn Gly Lys Glu Ile Ala Arg Asp Gln Val Thr
        675                 680                 685
```

-continued

Thr Ala Gly Ala Pro Ala Ala Val Lys Leu Thr Ala Asp Arg Lys Val
690                 695                 700

Ile Lys Ala Asp Gly Thr Asp Leu Ser Phe Ile Thr Ala Glu Ile Val
705                 710                 715                 720

Asp Ser Lys Gly Asn Val Val Pro Asn Ala Asp His Leu Ile Gln Phe
            725                 730                 735

His Leu Ser Gly His Gly Glu Leu Ala Gly Val Asp Asn Gly Asp Ala
        740                 745                 750

Ala Ser Val Glu Arg Tyr Lys Asp Asn Lys Arg Lys Ala Phe Ser Gly
        755                 760                 765

Lys Ala Leu Ala Ile Val Gln Ser Asn Lys Leu Asp Gly Asn Ile Thr
770                 775                 780

Leu His Ala Ser Ala Glu Gly Leu Ser Ser Gly Asn Val Thr Ile Phe
785                 790                 795                 800

Thr Thr Ala Ser Ala Asp Gln Asn Ser Ile Thr Ile Ala Gly Ile Asp
            805                 810                 815

Glu Val Asn Val Leu Val Asp Phe Asn Val Val Pro Glu Leu Pro Ser
            820                 825                 830

Gln Ile Lys Val Tyr Tyr Ser Asp Ser Thr Val Glu Met Lys Pro Val
    835                 840                 845

Thr Trp Asp Ala Val Asp Pro Asn Leu Leu Asn Thr Ala Gly Lys Ile
    850                 855                 860

Ile Val Glu Gly Thr Val Gly Thr Asp Lys Lys Ala Lys Ala Leu
865                 870                 875                 880

Leu Ile Val Lys Gly Asn Gly Gln Glu Asn Ser Glu Tyr Arg Ile Asp
                885                 890                 895

Leu Phe Ser Pro Asp Pro Lys Leu Ile Ser Thr Glu Leu Thr Val Glu
            900                 905                 910

Lys Thr Asn Ile Met Glu Asp Asp Phe Ile Asp Ile Lys Val Ile Gly
        915                 920                 925

Gln Leu Glu Asn Lys Glu Val Val Asp Leu Ser Asn Phe Met Pro Ile
930                 935                 940

Tyr Glu Phe Asp Cys Asp Ile Ile Lys Ile Gly Asn Lys Leu Tyr
945                 950                 955                 960

Ala Leu Glu Glu Gly Leu Val Lys Val Thr Ala Ala Val Thr Tyr Lys
            965                 970                 975

Gly Arg Thr Val Thr Ser Pro Glu Met Met Leu Lys Ile Thr Lys Asn
            980                 985                 990

Pro Val Pro Lys Thr Ile Thr His Ile Asp Ser Ile Thr Val Val Ala
        995                 1000                1005

Gly Lys Gly Glu Ala Pro Val Leu Pro Ala Thr Ala Val Ala His
    1010                1015                1020

Phe Asp Arg Gly Met Pro Arg Asp Val Lys Val Lys Trp Glu Ile
    1025                1030                1035

Val Asn Pro Ala Leu Tyr Gln Asn Leu Gly Glu Phe Thr Val Ser
    1040                1045                1050

Gly Asp Val Glu Gly Thr Glu Ile Lys Ala Gln Ala Lys Val Met
    1055                1060                1065

Val Arg Ser Ala Leu Ala Ile Glu Thr Ile Ser Met Ala Val Leu
    1070                1075                1080

Pro Asn Gln Lys Pro Glu Leu Pro Gln Lys Val Thr Val Tyr Tyr
    1085                1090                1095

```
Ser Asp Gly Thr Glu Glu Gln Ala Asp Val Asp Trp Asp Ala Met
    1100            1105                1110
Pro Ser Ala Glu Leu Lys Ser Glu Gly Val Val Lys Val Lys Gly
    1115            1120                1125
Ser Val Lys Gly Val Asp Leu Lys Ala Thr Ala Gln Ile Arg Val
    1130            1135                1140
Thr Ser Glu Val Gly Gly Val Gln Asn Ile Ser Arg Ala Lys Asn
    1145            1150                1155
Gly Tyr Glu Tyr Pro Lys Ala Glu Ala Ser Phe Thr Asn Thr Gly
    1160            1165                1170
Pro Gly Ser Asn Asp Arg Ile Glu Ala Ile Asn Asp Val Ile
    1175            1180                1185
Ser Tyr Asp Ala Glu Pro His Asn Arg Trp Thr Asn Trp Gln Pro
    1190            1195                1200
Thr Pro Arg Pro Gly Asp Trp Val Ser Ile Thr Phe Gly Asp Ser
    1205            1210                1215
Lys Pro Arg Lys Tyr Asp Ile Asp Ser Met Glu Ile His Trp Tyr
    1220            1225                1230
Glu Asp Leu Gly Thr Ser Ser Pro Ala Tyr Phe Arg Ile Gln Tyr
    1235            1240                1245
Lys Ser Gly Asp Glu Trp Lys Asp Val Ser Gly Leu Lys Thr Asn
    1250            1255                1260
Pro Ser Asn Thr Val Leu Arg Gln Ala Asn Val Tyr Thr Phe Asp
    1265            1270                1275
Lys Val Arg Thr Ser Ala Ile Arg Val Asp Met Thr Ala Lys Thr
    1280            1285                1290
Gly Lys Ser Leu Ala Ile Thr Glu Ile Lys Val Phe Ser Lys Trp
    1295            1300                1305
Ala Lys Ala His Thr His Pro Met Val Thr Asp Ile Lys Leu Gly
    1310            1315                1320
Asp Leu Ser Ile Leu Asp Asp Phe Ser Lys Lys Gly Asp Asn Asn
    1325            1330                1335
Glu Leu Thr Phe Gln Val Lys Asp Pro Arg Asp Ile Pro Glu Ile
    1340            1345                1350
Lys Val Lys Ala Glu Asp Asn Thr Ser Ile Thr Ile Ile Pro Thr
    1355            1360                1365
Phe Thr Ala Pro Ser Thr Ala Lys Ile Ile Ala Lys Ser Glu Asp
    1370            1375                1380
Gly Met Lys Val Glu Ile Tyr Asn Ile Arg Phe Thr Glu
    1385            1390                1395

<210> SEQ ID NO 4
<211> LENGTH: 799
<212> TYPE: PRT
<213> ORGANISM: Artificial Sequence
<220> FEATURE:
<223> OTHER INFORMATION: BgaII-799

<400> SEQUENCE: 4

Met Arg Arg Ile Asn Phe Asn Asp Asn Trp Arg Phe Gln Arg Glu Ile
1               5                   10                  15
Ser Thr Ser Leu Arg Glu Ala Gln Lys Pro Ser Phe Asn Asp His Ser
                20                  25                  30
Trp Arg Gln Leu Ser Leu Pro Asp Trp Ser Ile Glu Leu Asp Phe
            35                  40                  45
```

-continued

```
Asn Lys Asp Ser Leu Ala Thr His Glu Gly Gly Tyr Leu Asp Gly Gly
    50                  55                  60

Val Gly Trp Tyr Arg Lys Thr Phe Thr Val Pro Ser Ala Met Glu Gly
65                  70                  75                  80

Lys Arg Ile Ser Leu Asp Phe Asp Gly Val Tyr Met Asn Ser Thr Thr
                85                  90                  95

Tyr Leu Asn Gly Glu Glu Leu Gly Thr Tyr Pro Phe Gly Tyr Asn Ala
            100                 105                 110

Phe Ser Tyr Asp Ile Thr Asp Lys Leu Phe Met Asp Gly Arg Glu Asn
        115                 120                 125

Val Leu Ala Val Lys Val Asp Asn Thr Gln Pro Ser Ser Arg Trp Tyr
130                 135                 140

Ser Gly Ser Gly Ile Tyr Arg Asn Val Tyr Leu Thr Val Thr Asn Pro
145                 150                 155                 160

Val His Val Ala Arg Tyr Gly Thr Phe Val Thr Thr Pro Asp Leu Glu
                165                 170                 175

Ser Ala Tyr Ala Ala Arg Lys Ala Glu Val Asn Ile Lys Thr Lys Ile
            180                 185                 190

Asn Asn Asp Ser Asp Ala Ala Val Gln Val Lys Val Lys Ser Thr Ile
        195                 200                 205

Tyr Asp Thr Asp Gly Lys Glu Val Ala Ser Val Val Ser Gln Glu Lys
    210                 215                 220

Thr Ala Ala Ala Gly Thr Thr Ala His Phe Glu Asp Asn Thr Val Ile
225                 230                 235                 240

Glu Asn Pro Glu Leu Trp Ser Leu Asp Asn Pro Tyr Arg Tyr Lys Leu
                245                 250                 255

Val Thr Asp Val Leu Ile Gly Gly Thr Val Asp Thr Tyr Glu Thr
            260                 265                 270

Arg Phe Gly Ala Arg Phe Phe Lys Phe Asp Ala Asn Glu Gly Phe Ser
    275                 280                 285

Leu Asn Gly Lys Pro Met Lys Leu Tyr Gly Val Ser Met His His Asp
    290                 295                 300

Leu Gly Ala Leu Gly Ala Ala Thr Asn Ala Arg Ala Val Glu Arg Gln
305                 310                 315                 320

Leu Gln Ile Met Lys Asp Met Gly Val Asn Ala Ile Arg Gly Thr His
                325                 330                 335

Asn Pro Val Ser Pro Glu Phe Leu Glu Ala Val Asn Asn Leu Gly Leu
            340                 345                 350

Leu Leu Ile Glu Glu Ala Phe Asp Cys Trp Ser Gln Ser Lys Lys Thr
        355                 360                 365

Tyr Asp Tyr Gly Arg Phe Phe Thr Arg Trp Ala Glu His Asp Val Lys
    370                 375                 380

Glu Met Val Asp Arg Gly Lys Asn Glu Pro Ser Ile Ile Met Trp Ser
385                 390                 395                 400

Ile Gly Asn Glu Ile Tyr Asp Thr Thr Ser Pro Ser Gly Val Glu Thr
                405                 410                 415

Ala Arg Asn Leu Val Arg Trp Ile Lys Glu Ile Asp Thr Thr Arg Pro
            420                 425                 430

Thr Thr Ile Gly Glu Asp Lys Thr Arg Gly Asp Lys Val Asn Val Thr
        435                 440                 445

Pro Ile Asp Pro Asn Ile Leu Glu Ile Phe His Thr Val Asp Val Val
    450                 455                 460

Gly Leu Asn Tyr Ser Glu Asn Asn Tyr Val Gly Tyr His Glu Gln His
```

```
               465                 470                 475                 480

Pro Asn Trp Lys Leu Tyr Gly Ser Glu Thr Ser Ser Ala Thr Arg Ser
                        485                 490                 495

Arg Gly Val Tyr Thr His Pro Tyr Glu Tyr Asn Leu Gly Thr Lys Tyr
                        500                 505                 510

Asp Leu Gln Gln Ser Ser Tyr Asp Asn Asp Tyr Val Pro Trp Gly
                    515                 520                 525

Arg Thr Ala Glu Asp Ala Trp Lys Ser Asp Arg Asp Leu Lys His Phe
                    530                 535                 540

Ala Gly Gln Phe Ile Trp Thr Gly Phe Asp Tyr Ile Gly Glu Pro Thr
        545                 550                 555                 560

Pro Tyr Tyr Asp Ser Tyr Pro Ala Lys Ser Ser Tyr Phe Gly Ala Val
                        565                 570                 575

Asp Thr Ala Gly Phe Pro Lys Asp Ile Phe Tyr Tyr Gln Ser Gln
                    580                 585                 590

Trp Lys Lys Glu Pro Met Val His Leu Leu Pro His Trp Asn Trp Thr
                    595                 600                 605

Glu Gly Glu Pro Val Arg Val Leu Ala Tyr Thr Asn Ala His Gln Val
                610                 615                 620

Glu Leu Phe Leu Asn Gly Lys Ser Leu Gly Val Arg Gly Tyr Glu Asn
        625                 630                 635                 640

Lys Lys Thr Ser Trp Gly Ala Pro Tyr Lys Glu Thr Lys Asp Gly Lys
                        645                 650                 655

Thr Tyr Leu Glu Trp Ala Val Pro Phe Lys Ala Gly Thr Leu Glu Ala
                    660                 665                 670

Val Ala Met Asp Glu Asn Gly Lys Glu Ile Ala Arg Asp Gln Val Thr
                    675                 680                 685

Thr Ala Gly Ala Pro Ala Ala Val Lys Leu Thr Ala Asp Arg Lys Val
                    690                 695                 700

Ile Lys Ala Asp Gly Thr Asp Leu Ser Phe Ile Thr Ala Glu Ile Val
        705                 710                 715                 720

Asp Ser Lys Gly Asn Val Val Pro Asn Ala Asp His Leu Ile Gln Phe
                        725                 730                 735

His Leu Ser Gly His Gly Glu Leu Ala Gly Val Asp Asn Gly Asp Ala
                    740                 745                 750

Ala Ser Val Glu Arg Tyr Lys Asp Asn Lys Arg Lys Ala Phe Ser Gly
                    755                 760                 765

Lys Ala Leu Ala Ile Val Gln Ser Asn Lys Leu Asp Gly Asn Ile Thr
            770                 775                 780

Leu His Ala Ser Ala Glu Gly Leu Ser Ser Gly Asn Val Thr Ile
        785                 790                 795

<210> SEQ ID NO 5
<211> LENGTH: 41
<212> TYPE: DNA
<213> ORGANISM: Artificial Sequence
<220> FEATURE:
<223> OTHER INFORMATION: BgaII-799-D92-R

<400> SEQUENCE: 5
gcgaccggcg ctcagctgtt aaatggtcac gttgccgctt g                         41

<210> SEQ ID NO 6
<211> LENGTH: 873
<212> TYPE: PRT
<213> ORGANISM: Artificial Sequence
```

<220> FEATURE:
<223> OTHER INFORMATION: BgaII-873

<400> SEQUENCE: 6

Met Arg Arg Ile Asn Phe Asn Asp Asn Trp Arg Phe Gln Arg Glu Ile
1               5                   10                  15

Ser Thr Ser Leu Arg Glu Ala Gln Lys Pro Ser Phe Asn Asp His Ser
            20                  25                  30

Trp Arg Gln Leu Ser Leu Pro His Asp Trp Ser Ile Glu Leu Asp Phe
        35                  40                  45

Asn Lys Asp Ser Leu Ala Thr His Glu Gly Gly Tyr Leu Asp Gly Gly
    50                  55                  60

Val Gly Trp Tyr Arg Lys Thr Phe Thr Val Pro Ser Ala Met Glu Gly
65                  70                  75                  80

Lys Arg Ile Ser Leu Asp Phe Asp Gly Val Tyr Met Asn Ser Thr Thr
                85                  90                  95

Tyr Leu Asn Gly Glu Glu Leu Gly Thr Tyr Pro Phe Gly Tyr Asn Ala
            100                 105                 110

Phe Ser Tyr Asp Ile Thr Asp Lys Leu Phe Met Asp Gly Arg Glu Asn
        115                 120                 125

Val Leu Ala Val Lys Val Asp Asn Thr Gln Pro Ser Ser Arg Trp Tyr
    130                 135                 140

Ser Gly Ser Gly Ile Tyr Arg Asn Val Tyr Leu Thr Val Thr Asn Pro
145                 150                 155                 160

Val His Val Ala Arg Tyr Gly Thr Phe Val Thr Thr Pro Asp Leu Glu
                165                 170                 175

Ser Ala Tyr Ala Ala Arg Lys Ala Glu Val Asn Ile Lys Thr Lys Ile
            180                 185                 190

Asn Asn Asp Ser Asp Ala Ala Val Gln Val Lys Val Lys Ser Thr Ile
        195                 200                 205

Tyr Asp Thr Asp Gly Lys Glu Val Ala Ser Val Val Ser Gln Glu Lys
    210                 215                 220

Thr Ala Ala Gly Thr Thr Ala His Phe Glu Asp Asn Thr Val Ile
225                 230                 235                 240

Glu Asn Pro Glu Leu Trp Ser Leu Asp Asn Pro Tyr Arg Tyr Lys Leu
                245                 250                 255

Val Thr Asp Val Leu Ile Gly Gly Glu Thr Val Asp Thr Tyr Glu Thr
            260                 265                 270

Arg Phe Gly Ala Arg Phe Phe Lys Phe Asp Ala Asn Glu Gly Phe Ser
        275                 280                 285

Leu Asn Gly Lys Pro Met Lys Leu Tyr Gly Val Ser Met His His Asp
    290                 295                 300

Leu Gly Ala Leu Gly Ala Thr Asn Ala Arg Ala Val Glu Arg Gln
305                 310                 315                 320

Leu Gln Ile Met Lys Asp Met Gly Val Asn Ala Ile Arg Gly Thr His
                325                 330                 335

Asn Pro Val Ser Pro Glu Phe Leu Glu Ala Val Asn Asn Leu Gly Leu
            340                 345                 350

Leu Leu Ile Glu Glu Ala Phe Asp Cys Trp Ser Gln Ser Lys Lys Thr
        355                 360                 365

Tyr Asp Tyr Gly Arg Phe Phe Thr Arg Trp Ala Glu His Asp Val Lys
    370                 375                 380

Glu Met Val Asp Arg Gly Lys Asn Glu Pro Ser Ile Ile Met Trp Ser
385                 390                 395                 400

```
Ile Gly Asn Glu Ile Tyr Asp Thr Thr Ser Pro Ser Gly Val Glu Thr
            405                 410                 415

Ala Arg Asn Leu Val Arg Trp Ile Lys Glu Ile Asp Thr Thr Arg Pro
        420                 425                 430

Thr Thr Ile Gly Glu Asp Lys Thr Arg Gly Asp Lys Val Asn Val Thr
            435                 440                 445

Pro Ile Asp Pro Asn Ile Leu Glu Ile Phe His Thr Val Asp Val Val
    450                 455                 460

Gly Leu Asn Tyr Ser Glu Asn Asn Tyr Val Gly Tyr His Glu Gln His
465                 470                 475                 480

Pro Asn Trp Lys Leu Tyr Gly Ser Glu Thr Ser Ala Thr Arg Ser
                485                 490                 495

Arg Gly Val Tyr Thr His Pro Tyr Glu Tyr Asn Leu Gly Thr Lys Tyr
            500                 505                 510

Asp Asp Leu Gln Gln Ser Ser Tyr Asp Asn Asp Tyr Val Pro Trp Gly
            515                 520                 525

Arg Thr Ala Glu Asp Ala Trp Lys Ser Asp Arg Asp Leu Lys His Phe
        530                 535                 540

Ala Gly Gln Phe Ile Trp Thr Gly Phe Asp Tyr Ile Gly Glu Pro Thr
545                 550                 555                 560

Pro Tyr Tyr Asp Ser Tyr Pro Ala Lys Ser Ser Tyr Phe Gly Ala Val
                565                 570                 575

Asp Thr Ala Gly Phe Pro Lys Asp Ile Phe Tyr Tyr Gln Ser Gln
            580                 585                 590

Trp Lys Lys Glu Pro Met Val His Leu Leu Pro His Trp Asn Trp Thr
        595                 600                 605

Glu Gly Glu Pro Val Arg Val Leu Ala Tyr Thr Asn Ala His Gln Val
    610                 615                 620

Glu Leu Phe Leu Asn Gly Lys Ser Leu Gly Val Arg Gly Tyr Glu Asn
625                 630                 635                 640

Lys Lys Thr Ser Trp Gly Ala Pro Tyr Lys Glu Thr Lys Asp Gly Lys
                645                 650                 655

Thr Tyr Leu Glu Trp Ala Val Pro Phe Lys Ala Gly Thr Leu Glu Ala
            660                 665                 670

Val Ala Met Asp Glu Asn Gly Lys Glu Ile Ala Arg Asp Gln Val Thr
            675                 680                 685

Thr Ala Gly Ala Pro Ala Ala Val Lys Leu Thr Ala Asp Arg Lys Val
    690                 695                 700

Ile Lys Ala Asp Gly Thr Asp Leu Ser Phe Ile Thr Ala Glu Ile Val
705                 710                 715                 720

Asp Ser Lys Gly Asn Val Val Pro Asn Ala Asp His Leu Ile Gln Phe
                725                 730                 735

His Leu Ser Gly His Gly Glu Leu Ala Gly Val Asp Asn Gly Asp Ala
            740                 745                 750

Ala Ser Val Glu Arg Tyr Lys Asp Asn Lys Arg Lys Ala Phe Ser Gly
        755                 760                 765

Lys Ala Leu Ala Ile Val Gln Ser Asn Lys Leu Asp Gly Asn Ile Thr
    770                 775                 780

Leu His Ala Ser Ala Glu Gly Leu Ser Ser Gly Asn Val Thr Ile Phe
785                 790                 795                 800

Thr Thr Ala Ser Ala Asp Gln Asn Ser Ile Thr Ile Ala Gly Ile Asp
                805                 810                 815
```

```
Glu Val Asn Val Leu Val Asp Phe Asn Val Val Pro Glu Leu Pro Ser
            820                 825                 830

Gln Ile Lys Val Tyr Tyr Ser Asp Ser Thr Val Glu Met Lys Pro Val
        835                 840                 845

Thr Trp Asp Ala Val Asp Pro Asn Leu Leu Asn Thr Ala Gly Lys Ile
850                 855                 860

Ile Val Glu Gly Thr Val Glu Gly Thr
865                 870

<210> SEQ ID NO 7
<211> LENGTH: 41
<212> TYPE: DNA
<213> ORGANISM: Artificial Sequence
<220> FEATURE:
<223> OTHER INFORMATION: BgaII-873-D92-R

<400> SEQUENCE: 7
gcgaccggcg ctcagctgtt aagttccttc cacagtaccc t                    41

<210> SEQ ID NO 8
<211> LENGTH: 900
<212> TYPE: PRT
<213> ORGANISM: Artificial Sequence
<220> FEATURE:
<223> OTHER INFORMATION: BgaII-900

<400> SEQUENCE: 8

Met Arg Arg Ile Asn Phe Asn Asp Asn Trp Arg Phe Gln Arg Glu Ile
1               5                   10                  15

Ser Thr Ser Leu Arg Glu Ala Gln Lys Pro Ser Phe Asn Asp His Ser
            20                  25                  30

Trp Arg Gln Leu Ser Leu Pro His Asp Trp Ser Ile Glu Leu Asp Phe
        35                  40                  45

Asn Lys Asp Ser Leu Ala Thr His Glu Gly Gly Tyr Leu Asp Gly Gly
    50                  55                  60

Val Gly Trp Tyr Arg Lys Thr Phe Thr Val Pro Ser Ala Met Glu Gly
65                  70                  75                  80

Lys Arg Ile Ser Leu Asp Phe Asp Gly Val Tyr Met Asn Ser Thr Thr
                85                  90                  95

Tyr Leu Asn Gly Glu Glu Leu Gly Thr Tyr Pro Phe Gly Tyr Asn Ala
            100                 105                 110

Phe Ser Tyr Asp Ile Thr Asp Lys Leu Phe Met Asp Gly Arg Glu Asn
        115                 120                 125

Val Leu Ala Val Lys Val Asp Asn Thr Gln Pro Ser Ser Arg Trp Tyr
    130                 135                 140

Ser Gly Ser Gly Ile Tyr Arg Asn Val Tyr Leu Thr Val Thr Asn Pro
145                 150                 155                 160

Val His Val Ala Arg Tyr Gly Thr Phe Val Thr Thr Pro Asp Leu Glu
                165                 170                 175

Ser Ala Tyr Ala Ala Arg Lys Ala Glu Val Asn Ile Lys Thr Lys Ile
            180                 185                 190

Asn Asn Asp Ser Asp Ala Ala Val Gln Val Lys Val Lys Ser Thr Ile
        195                 200                 205

Tyr Asp Thr Asp Gly Lys Glu Val Ala Ser Val Val Ser Gln Glu Lys
    210                 215                 220

Thr Ala Ala Ala Gly Thr Thr Ala His Phe Glu Asp Asn Thr Val Ile
225                 230                 235                 240
```

```
Glu Asn Pro Glu Leu Trp Ser Leu Asp Asn Pro Tyr Arg Tyr Lys Leu
                245                 250                 255

Val Thr Asp Val Leu Ile Gly Gly Glu Thr Val Asp Thr Tyr Glu Thr
            260                 265                 270

Arg Phe Gly Ala Arg Phe Phe Lys Phe Asp Ala Asn Glu Gly Phe Ser
        275                 280                 285

Leu Asn Gly Lys Pro Met Lys Leu Tyr Gly Val Ser Met His His Asp
    290                 295                 300

Leu Gly Ala Leu Gly Ala Ala Thr Asn Ala Arg Ala Val Glu Arg Gln
305                 310                 315                 320

Leu Gln Ile Met Lys Asp Met Gly Val Asn Ala Ile Arg Gly Thr His
                325                 330                 335

Asn Pro Val Ser Pro Glu Phe Leu Glu Ala Val Asn Asn Leu Gly Leu
            340                 345                 350

Leu Leu Ile Glu Glu Ala Phe Asp Cys Trp Ser Gln Ser Lys Lys Thr
        355                 360                 365

Tyr Asp Tyr Gly Arg Phe Phe Thr Arg Trp Ala Glu His Asp Val Lys
    370                 375                 380

Glu Met Val Asp Arg Gly Lys Asn Glu Pro Ser Ile Ile Met Trp Ser
385                 390                 395                 400

Ile Gly Asn Glu Ile Tyr Asp Thr Thr Ser Pro Ser Gly Val Glu Thr
                405                 410                 415

Ala Arg Asn Leu Val Arg Trp Ile Lys Glu Ile Asp Thr Thr Arg Pro
            420                 425                 430

Thr Thr Ile Gly Glu Asp Lys Thr Arg Gly Asp Lys Val Asn Val Thr
        435                 440                 445

Pro Ile Asp Pro Asn Ile Leu Glu Ile Phe His Thr Val Asp Val Val
    450                 455                 460

Gly Leu Asn Tyr Ser Glu Asn Asn Tyr Val Gly Tyr His Glu Gln His
465                 470                 475                 480

Pro Asn Trp Lys Leu Tyr Gly Ser Glu Thr Ser Ser Ala Thr Arg Ser
                485                 490                 495

Arg Gly Val Tyr Thr His Pro Tyr Glu Tyr Asn Leu Gly Thr Lys Tyr
            500                 505                 510

Asp Asp Leu Gln Gln Ser Ser Tyr Asp Asn Asp Tyr Val Pro Trp Gly
        515                 520                 525

Arg Thr Ala Glu Asp Ala Trp Lys Ser Asp Arg Asp Leu Lys His Phe
    530                 535                 540

Ala Gly Gln Phe Ile Trp Thr Gly Phe Asp Tyr Ile Gly Glu Pro Thr
545                 550                 555                 560

Pro Tyr Tyr Asp Ser Tyr Pro Ala Lys Ser Ser Tyr Phe Gly Ala Val
                565                 570                 575

Asp Thr Ala Gly Phe Pro Lys Asp Ile Phe Tyr Tyr Gln Ser Gln
            580                 585                 590

Trp Lys Lys Glu Pro Met Val His Leu Leu Pro His Trp Asn Trp Thr
        595                 600                 605

Glu Gly Glu Pro Val Arg Val Leu Ala Tyr Thr Asn Ala His Gln Val
    610                 615                 620

Glu Leu Phe Leu Asn Gly Lys Ser Leu Gly Val Arg Gly Tyr Glu Asn
625                 630                 635                 640

Lys Lys Thr Ser Trp Gly Ala Pro Tyr Lys Glu Thr Lys Asp Gly Lys
                645                 650                 655

Thr Tyr Leu Glu Trp Ala Val Pro Phe Lys Ala Gly Thr Leu Glu Ala
```

```
            660                 665                 670
Val Ala Met Asp Glu Asn Gly Lys Glu Ile Ala Arg Asp Gln Val Thr
            675                 680                 685

Thr Ala Gly Ala Pro Ala Ala Val Lys Leu Thr Ala Asp Arg Lys Val
        690                 695                 700

Ile Lys Ala Asp Gly Thr Asp Leu Ser Phe Ile Thr Ala Glu Ile Val
705                 710                 715                 720

Asp Ser Lys Gly Asn Val Val Pro Asn Ala Asp His Leu Ile Gln Phe
                725                 730                 735

His Leu Ser Gly His Gly Glu Leu Ala Gly Val Asp Asn Gly Asp Ala
            740                 745                 750

Ala Ser Val Glu Arg Tyr Lys Asp Asn Lys Arg Lys Ala Phe Ser Gly
        755                 760                 765

Lys Ala Leu Ala Ile Val Gln Ser Asn Lys Leu Asp Gly Asn Ile Thr
    770                 775                 780

Leu His Ala Ser Ala Glu Gly Leu Ser Ser Gly Asn Val Thr Ile Phe
785                 790                 795                 800

Thr Thr Ala Ser Ala Asp Gln Asn Ser Ile Thr Ile Ala Gly Ile Asp
                805                 810                 815

Glu Val Asn Val Leu Val Asp Phe Asn Val Val Pro Glu Leu Pro Ser
            820                 825                 830

Gln Ile Lys Val Tyr Tyr Ser Asp Ser Thr Val Glu Met Lys Pro Val
        835                 840                 845

Thr Trp Asp Ala Val Asp Pro Asn Leu Leu Asn Thr Ala Gly Lys Ile
    850                 855                 860

Ile Val Glu Gly Thr Val Gly Thr Asp Lys Lys Ala Lys Ala Leu
865                 870                 875                 880

Leu Ile Val Lys Gly Asn Gly Gln Glu Asn Ser Glu Tyr Arg Ile Asp
                885                 890                 895

Leu Phe Ser Pro
            900

<210> SEQ ID NO 9
<211> LENGTH: 41
<212> TYPE: DNA
<213> ORGANISM: Artificial Sequence
<220> FEATURE:
<223> OTHER INFORMATION: BgaII-900-D92-R

<400> SEQUENCE: 9
gcgaccggcg ctcagctgtt atggcgagaa aagatcaatc c                    41

<210> SEQ ID NO 10
<211> LENGTH: 950
<212> TYPE: PRT
<213> ORGANISM: Artificial Sequence
<220> FEATURE:
<223> OTHER INFORMATION: BgaII-950

<400> SEQUENCE: 10

Met Arg Arg Ile Asn Phe Asn Asp Asn Trp Arg Phe Gln Arg Glu Ile
1               5                   10                  15

Ser Thr Ser Leu Arg Glu Ala Gln Lys Pro Ser Phe Asn Asp His Ser
            20                  25                  30

Trp Arg Gln Leu Ser Leu Pro His Asp Trp Ser Ile Glu Leu Asp Phe
        35                  40                  45

Asn Lys Asp Ser Leu Ala Thr His Glu Gly Gly Tyr Leu Asp Gly Gly
```

-continued

```
             50                  55                  60
Val Gly Trp Tyr Arg Lys Thr Phe Thr Val Pro Ser Ala Met Glu Gly
 65                  70                  75                  80

Lys Arg Ile Ser Leu Asp Phe Asp Gly Val Tyr Met Asn Ser Thr Thr
                 85                  90                  95

Tyr Leu Asn Gly Glu Leu Gly Thr Tyr Pro Phe Gly Tyr Asn Ala
                100                 105                 110

Phe Ser Tyr Asp Ile Thr Asp Lys Leu Phe Met Asp Gly Arg Glu Asn
                115                 120                 125

Val Leu Ala Val Lys Val Asp Asn Thr Gln Pro Ser Ser Arg Trp Tyr
                130                 135                 140

Ser Gly Ser Gly Ile Tyr Arg Asn Val Tyr Leu Thr Val Thr Asn Pro
145                 150                 155                 160

Val His Val Ala Arg Tyr Gly Thr Phe Val Thr Thr Pro Asp Leu Glu
                165                 170                 175

Ser Ala Tyr Ala Ala Arg Lys Ala Glu Val Asn Ile Lys Thr Lys Ile
                180                 185                 190

Asn Asn Asp Ser Asp Ala Ala Val Gln Val Lys Val Lys Ser Thr Ile
                195                 200                 205

Tyr Asp Thr Asp Gly Lys Glu Val Ala Ser Val Val Ser Gln Glu Lys
210                 215                 220

Thr Ala Ala Gly Thr Thr Ala His Phe Glu Asp Asn Thr Val Ile
225                 230                 235                 240

Glu Asn Pro Glu Leu Trp Ser Leu Asp Asn Pro Tyr Arg Tyr Lys Leu
                245                 250                 255

Val Thr Asp Val Leu Ile Gly Gly Glu Thr Val Asp Thr Tyr Glu Thr
                260                 265                 270

Arg Phe Gly Ala Arg Phe Phe Lys Phe Asp Ala Asn Glu Gly Phe Ser
                275                 280                 285

Leu Asn Gly Lys Pro Met Lys Leu Tyr Gly Val Ser Met His His Asp
                290                 295                 300

Leu Gly Ala Leu Gly Ala Ala Thr Asn Ala Arg Ala Val Glu Arg Gln
305                 310                 315                 320

Leu Gln Ile Met Lys Asp Met Gly Val Asn Ala Ile Arg Gly Thr His
                325                 330                 335

Asn Pro Val Ser Pro Glu Phe Leu Glu Ala Val Asn Asn Leu Gly Leu
                340                 345                 350

Leu Leu Ile Glu Glu Ala Phe Asp Cys Trp Ser Gln Ser Lys Lys Thr
                355                 360                 365

Tyr Asp Tyr Gly Arg Phe Phe Thr Arg Trp Ala Glu His Asp Val Lys
                370                 375                 380

Glu Met Val Asp Arg Gly Lys Asn Glu Pro Ser Ile Ile Met Trp Ser
385                 390                 395                 400

Ile Gly Asn Glu Ile Tyr Asp Thr Thr Ser Pro Ser Gly Val Glu Thr
                405                 410                 415

Ala Arg Asn Leu Val Arg Trp Ile Lys Glu Ile Asp Thr Thr Arg Pro
                420                 425                 430

Thr Thr Ile Gly Glu Asp Lys Thr Arg Gly Asp Lys Val Asn Val Thr
                435                 440                 445

Pro Ile Asp Pro Asn Ile Leu Glu Ile Phe His Thr Val Asp Val Val
                450                 455                 460

Gly Leu Asn Tyr Ser Glu Asn Asn Tyr Val Gly Tyr His Glu Gln His
465                 470                 475                 480
```

-continued

```
Pro Asn Trp Lys Leu Tyr Gly Ser Glu Thr Ser Ser Ala Thr Arg Ser
            485                 490                 495

Arg Gly Val Tyr Thr His Pro Tyr Glu Tyr Asn Leu Gly Thr Lys Tyr
            500                 505                 510

Asp Asp Leu Gln Gln Ser Ser Tyr Asp Asn Asp Tyr Val Pro Trp Gly
            515                 520                 525

Arg Thr Ala Glu Asp Ala Trp Lys Ser Asp Arg Asp Leu Lys His Phe
            530                 535                 540

Ala Gly Gln Phe Ile Trp Thr Gly Phe Asp Tyr Ile Gly Glu Pro Thr
545                 550                 555                 560

Pro Tyr Tyr Asp Ser Tyr Pro Ala Lys Ser Ser Tyr Phe Gly Ala Val
            565                 570                 575

Asp Thr Ala Gly Phe Pro Lys Asp Ile Phe Tyr Tyr Gln Ser Gln
            580                 585                 590

Trp Lys Lys Glu Pro Met Val His Leu Leu Pro His Trp Asn Trp Thr
            595                 600                 605

Glu Gly Glu Pro Val Arg Val Leu Ala Tyr Thr Asn Ala His Gln Val
            610                 615                 620

Glu Leu Phe Leu Asn Gly Lys Ser Leu Gly Val Arg Gly Tyr Glu Asn
625                 630                 635                 640

Lys Lys Thr Ser Trp Gly Ala Pro Tyr Lys Glu Thr Lys Asp Gly Lys
            645                 650                 655

Thr Tyr Leu Glu Trp Ala Val Pro Phe Lys Ala Gly Thr Leu Glu Ala
            660                 665                 670

Val Ala Met Asp Glu Asn Gly Lys Glu Ile Ala Arg Asp Gln Val Thr
            675                 680                 685

Thr Ala Gly Ala Pro Ala Ala Val Lys Leu Thr Ala Asp Arg Lys Val
            690                 695                 700

Ile Lys Ala Asp Gly Thr Asp Leu Ser Phe Ile Thr Ala Glu Ile Val
705                 710                 715                 720

Asp Ser Lys Gly Asn Val Val Pro Asn Ala Asp His Leu Ile Gln Phe
            725                 730                 735

His Leu Ser Gly His Gly Glu Leu Ala Gly Val Asp Asn Gly Asp Ala
            740                 745                 750

Ala Ser Val Glu Arg Tyr Lys Asp Asn Lys Arg Lys Ala Phe Ser Gly
            755                 760                 765

Lys Ala Leu Ala Ile Val Gln Ser Asn Lys Leu Asp Gly Asn Ile Thr
            770                 775                 780

Leu His Ala Ser Ala Glu Gly Leu Ser Ser Gly Asn Val Thr Ile Phe
785                 790                 795                 800

Thr Thr Ala Ser Ala Asp Gln Asn Ser Ile Thr Ile Ala Gly Ile Asp
            805                 810                 815

Glu Val Asn Val Leu Val Asp Phe Asn Val Val Pro Glu Leu Pro Ser
            820                 825                 830

Gln Ile Lys Val Tyr Tyr Ser Asp Ser Thr Val Glu Met Lys Pro Val
            835                 840                 845

Thr Trp Asp Ala Val Asp Pro Asn Leu Leu Asn Thr Ala Gly Lys Ile
            850                 855                 860

Ile Val Glu Gly Thr Val Glu Gly Thr Asp Lys Lys Ala Lys Ala Leu
865                 870                 875                 880

Leu Ile Val Lys Gly Asn Gly Gln Glu Asn Ser Glu Tyr Arg Ile Asp
            885                 890                 895
```

```
Leu Phe Ser Pro Asp Pro Lys Leu Ile Ser Thr Glu Leu Thr Val Glu
                900                 905                 910

Lys Thr Asn Ile Met Glu Asp Asp Phe Ile Asp Ile Lys Val Ile Gly
            915                 920                 925

Gln Leu Glu Asn Lys Glu Val Val Asp Leu Ser Asn Phe Met Pro Ile
        930                 935                 940

Tyr Glu Phe Asp Cys Asp
945                 950
```

<210> SEQ ID NO 11
<211> LENGTH: 41
<212> TYPE: DNA
<213> ORGANISM: Artificial Sequence
<220> FEATURE:
<223> OTHER INFORMATION: BgaII-950-D92-R

<400> SEQUENCE: 11
gcgaccggcg ctcagctgtt aatcgcagtc gaattcatag a          41

<210> SEQ ID NO 12
<211> LENGTH: 1000
<212> TYPE: PRT
<213> ORGANISM: Artificial Sequence
<220> FEATURE:
<223> OTHER INFORMATION: BgaII-1000

<400> SEQUENCE: 12

```
Met Arg Arg Ile Asn Phe Asn Asp Asn Trp Arg Phe Gln Arg Glu Ile
1               5                   10                  15

Ser Thr Ser Leu Arg Glu Ala Gln Lys Pro Ser Phe Asn Asp His Ser
            20                  25                  30

Trp Arg Gln Leu Ser Leu Pro His Asp Trp Ser Ile Glu Leu Asp Phe
        35                  40                  45

Asn Lys Asp Ser Leu Ala Thr His Glu Gly Gly Tyr Leu Asp Gly Gly
    50                  55                  60

Val Gly Trp Tyr Arg Lys Thr Phe Thr Val Pro Ser Ala Met Glu Gly
65                  70                  75                  80

Lys Arg Ile Ser Leu Asp Phe Asp Gly Val Tyr Met Asn Ser Thr Thr
                85                  90                  95

Tyr Leu Asn Gly Glu Glu Leu Gly Thr Tyr Pro Phe Gly Tyr Asn Ala
            100                 105                 110

Phe Ser Tyr Asp Ile Thr Asp Lys Leu Phe Met Asp Gly Arg Glu Asn
        115                 120                 125

Val Leu Ala Val Lys Val Asp Asn Thr Gln Pro Ser Ser Arg Trp Tyr
    130                 135                 140

Ser Gly Ser Gly Ile Tyr Arg Asn Val Tyr Leu Thr Val Thr Asn Pro
145                 150                 155                 160

Val His Val Ala Arg Tyr Gly Thr Phe Val Thr Thr Pro Asp Leu Glu
                165                 170                 175

Ser Ala Tyr Ala Ala Arg Lys Ala Glu Val Asn Ile Lys Thr Lys Ile
            180                 185                 190

Asn Asn Asp Ser Asp Ala Ala Val Gln Val Lys Val Lys Ser Thr Ile
        195                 200                 205

Tyr Asp Thr Asp Gly Lys Glu Val Ala Ser Val Val Ser Gln Glu Lys
    210                 215                 220

Thr Ala Ala Ala Gly Thr Thr Ala His Phe Glu Asp Asn Thr Val Ile
225                 230                 235                 240
```

-continued

```
Glu Asn Pro Glu Leu Trp Ser Leu Asp Asn Pro Tyr Arg Tyr Lys Leu
                245                 250                 255
Val Thr Asp Val Leu Ile Gly Gly Glu Thr Val Asp Thr Tyr Glu Thr
            260                 265                 270
Arg Phe Gly Ala Arg Phe Phe Lys Phe Asp Ala Asn Glu Gly Phe Ser
        275                 280                 285
Leu Asn Gly Lys Pro Met Lys Leu Tyr Gly Val Ser Met His His Asp
    290                 295                 300
Leu Gly Ala Leu Gly Ala Ala Thr Asn Ala Arg Ala Val Glu Arg Gln
305                 310                 315                 320
Leu Gln Ile Met Lys Asp Met Gly Val Asn Ala Ile Arg Gly Thr His
                325                 330                 335
Asn Pro Val Ser Pro Glu Phe Leu Glu Ala Val Asn Asn Leu Gly Leu
            340                 345                 350
Leu Leu Ile Glu Glu Ala Phe Asp Cys Trp Ser Gln Ser Lys Lys Thr
        355                 360                 365
Tyr Asp Tyr Gly Arg Phe Phe Thr Arg Trp Ala Glu His Asp Val Lys
    370                 375                 380
Glu Met Val Asp Arg Gly Lys Asn Glu Pro Ser Ile Ile Met Trp Ser
385                 390                 395                 400
Ile Gly Asn Glu Ile Tyr Asp Thr Thr Ser Pro Ser Gly Val Glu Thr
                405                 410                 415
Ala Arg Asn Leu Val Arg Trp Ile Lys Glu Ile Asp Thr Thr Arg Pro
            420                 425                 430
Thr Thr Ile Gly Glu Asp Lys Thr Arg Gly Asp Lys Val Asn Val Thr
        435                 440                 445
Pro Ile Asp Pro Asn Ile Leu Glu Ile Phe His Thr Val Asp Val Val
    450                 455                 460
Gly Leu Asn Tyr Ser Glu Asn Asn Tyr Val Gly Tyr His Glu Gln His
465                 470                 475                 480
Pro Asn Trp Lys Leu Tyr Gly Ser Glu Thr Ser Ser Ala Thr Arg Ser
                485                 490                 495
Arg Gly Val Tyr Thr His Pro Tyr Glu Tyr Asn Leu Gly Thr Lys Tyr
            500                 505                 510
Asp Asp Leu Gln Gln Ser Ser Tyr Asp Asn Asp Tyr Val Pro Trp Gly
        515                 520                 525
Arg Thr Ala Glu Asp Ala Trp Lys Ser Asp Arg Asp Leu Lys His Phe
    530                 535                 540
Ala Gly Gln Phe Ile Trp Thr Gly Phe Asp Tyr Ile Gly Glu Pro Thr
545                 550                 555                 560
Pro Tyr Tyr Asp Ser Tyr Pro Ala Lys Ser Ser Tyr Phe Gly Ala Val
                565                 570                 575
Asp Thr Ala Gly Phe Pro Lys Asp Ile Phe Tyr Tyr Gln Ser Gln
            580                 585                 590
Trp Lys Lys Glu Pro Met Val His Leu Leu Pro His Trp Asn Trp Thr
        595                 600                 605
Glu Gly Glu Pro Val Arg Val Leu Ala Tyr Thr Asn Ala His Gln Val
    610                 615                 620
Glu Leu Phe Leu Asn Gly Lys Ser Leu Gly Val Arg Gly Tyr Glu Asn
625                 630                 635                 640
Lys Lys Thr Ser Trp Gly Ala Pro Tyr Lys Glu Thr Lys Asp Gly Lys
                645                 650                 655
Thr Tyr Leu Glu Trp Ala Val Pro Phe Lys Ala Gly Thr Leu Glu Ala
```

660                 665                 670
Val Ala Met Asp Glu Asn Gly Lys Glu Ile Ala Arg Asp Gln Val Thr
            675                 680                 685

Thr Ala Gly Ala Pro Ala Ala Val Lys Leu Thr Ala Asp Arg Lys Val
        690                 695                 700

Ile Lys Ala Asp Gly Thr Asp Leu Ser Phe Ile Thr Ala Glu Ile Val
705                 710                 715                 720

Asp Ser Lys Gly Asn Val Val Pro Asn Ala Asp His Leu Ile Gln Phe
                725                 730                 735

His Leu Ser Gly His Gly Glu Leu Ala Gly Val Asp Asn Gly Asp Ala
            740                 745                 750

Ala Ser Val Glu Arg Tyr Lys Asp Asn Lys Arg Lys Ala Phe Ser Gly
        755                 760                 765

Lys Ala Leu Ala Ile Val Gln Ser Asn Lys Leu Asp Gly Asn Ile Thr
        770                 775                 780

Leu His Ala Ser Ala Glu Gly Leu Ser Ser Gly Asn Val Thr Ile Phe
785                 790                 795                 800

Thr Thr Ala Ser Ala Asp Gln Asn Ser Ile Thr Ile Ala Gly Ile Asp
            805                 810                 815

Glu Val Asn Val Leu Val Asp Phe Asn Val Val Pro Glu Leu Pro Ser
        820                 825                 830

Gln Ile Lys Val Tyr Tyr Ser Asp Ser Thr Val Glu Met Lys Pro Val
        835                 840                 845

Thr Trp Asp Ala Val Asp Pro Asn Leu Leu Asn Thr Ala Gly Lys Ile
        850                 855                 860

Ile Val Glu Gly Thr Val Gly Thr Asp Lys Lys Ala Lys Ala Leu
865                 870                 875                 880

Leu Ile Val Lys Gly Asn Gly Gln Glu Asn Ser Glu Tyr Arg Ile Asp
                885                 890                 895

Leu Phe Ser Pro Asp Pro Lys Leu Ile Ser Thr Glu Leu Thr Val Glu
            900                 905                 910

Lys Thr Asn Ile Met Glu Asp Asp Phe Ile Asp Ile Lys Val Ile Gly
        915                 920                 925

Gln Leu Glu Asn Lys Glu Val Val Asp Leu Ser Asn Phe Met Pro Ile
        930                 935                 940

Tyr Glu Phe Asp Cys Asp Ile Ile Lys Ile Glu Gly Asn Lys Leu Tyr
945                 950                 955                 960

Ala Leu Glu Glu Gly Leu Val Lys Val Thr Ala Ala Val Thr Tyr Lys
                965                 970                 975

Gly Arg Thr Val Thr Ser Pro Glu Met Met Leu Lys Ile Thr Lys Asn
            980                 985                 990

Pro Val Pro Lys Thr Ile Thr His
        995                 1000

<210> SEQ ID NO 13
<211> LENGTH: 41
<212> TYPE: DNA
<213> ORGANISM: Artificial Sequence
<220> FEATURE:
<223> OTHER INFORMATION: BgaII-1000-D92-R

<400> SEQUENCE: 13
gcgaccggcg ctcagctgtt agtgcgtaat ggttttaggg a        41

<210> SEQ ID NO 14

```
<211> LENGTH: 1059
<212> TYPE: PRT
<213> ORGANISM: Artificial Sequence
<220> FEATURE:
<223> OTHER INFORMATION: BgaII-1059

<400> SEQUENCE: 14
```

Met Arg Arg Ile Asn Phe Asn Asp Asn Trp Arg Phe Gln Arg Glu Ile
1               5                   10                  15

Ser Thr Ser Leu Arg Glu Ala Gln Lys Pro Ser Phe Asn Asp His Ser
            20                  25                  30

Trp Arg Gln Leu Ser Leu Pro His Asp Trp Ser Ile Glu Leu Asp Phe
        35                  40                  45

Asn Lys Asp Ser Leu Ala Thr His Glu Gly Gly Tyr Leu Asp Gly Gly
    50                  55                  60

Val Gly Trp Tyr Arg Lys Thr Phe Thr Val Pro Ser Ala Met Glu Gly
65                  70                  75                  80

Lys Arg Ile Ser Leu Asp Phe Asp Gly Val Tyr Met Asn Ser Thr Thr
                85                  90                  95

Tyr Leu Asn Gly Glu Glu Leu Gly Thr Tyr Pro Phe Gly Tyr Asn Ala
            100                 105                 110

Phe Ser Tyr Asp Ile Thr Asp Lys Leu Phe Met Asp Gly Arg Glu Asn
        115                 120                 125

Val Leu Ala Val Lys Val Asp Asn Thr Gln Pro Ser Ser Arg Trp Tyr
    130                 135                 140

Ser Gly Ser Gly Ile Tyr Arg Asn Val Tyr Leu Thr Val Thr Asn Pro
145                 150                 155                 160

Val His Val Ala Arg Tyr Gly Thr Phe Val Thr Thr Pro Asp Leu Glu
                165                 170                 175

Ser Ala Tyr Ala Ala Arg Lys Ala Glu Val Asn Ile Lys Thr Lys Ile
            180                 185                 190

Asn Asn Asp Ser Asp Ala Ala Val Gln Val Lys Val Lys Ser Thr Ile
        195                 200                 205

Tyr Asp Thr Asp Gly Lys Glu Val Ala Ser Val Val Ser Gln Glu Lys
    210                 215                 220

Thr Ala Ala Ala Gly Thr Thr Ala His Phe Glu Asp Asn Thr Val Ile
225                 230                 235                 240

Glu Asn Pro Glu Leu Trp Ser Leu Asp Asn Pro Tyr Arg Tyr Lys Leu
                245                 250                 255

Val Thr Asp Val Leu Ile Gly Gly Glu Thr Val Asp Thr Tyr Glu Thr
            260                 265                 270

Arg Phe Gly Ala Arg Phe Phe Lys Phe Asp Ala Asn Glu Gly Phe Ser
        275                 280                 285

Leu Asn Gly Lys Pro Met Lys Leu Tyr Gly Val Ser Met His His Asp
    290                 295                 300

Leu Gly Ala Leu Gly Ala Ala Thr Asn Ala Arg Ala Val Glu Arg Gln
305                 310                 315                 320

Leu Gln Ile Met Lys Asp Met Gly Val Asn Ala Ile Arg Gly Thr His
                325                 330                 335

Asn Pro Val Ser Pro Glu Phe Leu Glu Ala Val Asn Asn Leu Gly Leu
            340                 345                 350

Leu Leu Ile Glu Glu Ala Phe Asp Cys Trp Ser Gln Ser Lys Lys Thr
        355                 360                 365

Tyr Asp Tyr Gly Arg Phe Phe Thr Arg Trp Ala Glu His Asp Val Lys
    370                 375                 380

-continued

```
Glu Met Val Asp Arg Gly Lys Asn Glu Pro Ser Ile Ile Met Trp Ser
385                 390                 395                 400

Ile Gly Asn Glu Ile Tyr Asp Thr Thr Ser Pro Ser Gly Val Glu Thr
            405                 410                 415

Ala Arg Asn Leu Val Arg Trp Ile Lys Glu Ile Asp Thr Thr Arg Pro
        420                 425                 430

Thr Thr Ile Gly Glu Asp Lys Thr Arg Gly Asp Lys Val Asn Val Thr
            435                 440                 445

Pro Ile Asp Pro Asn Ile Leu Glu Ile Phe His Thr Val Asp Val Val
        450                 455                 460

Gly Leu Asn Tyr Ser Glu Asn Asn Tyr Val Gly Tyr His Glu Gln His
465                 470                 475                 480

Pro Asn Trp Lys Leu Tyr Gly Ser Glu Thr Ser Ala Thr Arg Ser
            485                 490                 495

Arg Gly Val Tyr Thr His Pro Tyr Glu Tyr Asn Leu Gly Thr Lys Tyr
            500                 505                 510

Asp Asp Leu Gln Gln Ser Ser Tyr Asp Asn Asp Tyr Val Pro Trp Gly
        515                 520                 525

Arg Thr Ala Glu Asp Ala Trp Lys Ser Asp Arg Asp Leu Lys His Phe
530                 535                 540

Ala Gly Gln Phe Ile Trp Thr Gly Phe Asp Tyr Ile Gly Glu Pro Thr
545                 550                 555                 560

Pro Tyr Tyr Asp Ser Tyr Pro Ala Lys Ser Ser Tyr Phe Gly Ala Val
            565                 570                 575

Asp Thr Ala Gly Phe Pro Lys Asp Ile Phe Tyr Tyr Gln Ser Gln
            580                 585                 590

Trp Lys Lys Glu Pro Met Val His Leu Leu Pro His Trp Asn Trp Thr
        595                 600                 605

Glu Gly Glu Pro Val Arg Val Leu Ala Tyr Thr Asn Ala His Gln Val
        610                 615                 620

Glu Leu Phe Leu Asn Gly Lys Ser Leu Gly Val Arg Gly Tyr Glu Asn
625                 630                 635                 640

Lys Lys Thr Ser Trp Gly Ala Pro Tyr Lys Glu Thr Lys Asp Gly Lys
            645                 650                 655

Thr Tyr Leu Glu Trp Ala Val Pro Phe Lys Ala Gly Thr Leu Glu Ala
            660                 665                 670

Val Ala Met Asp Glu Asn Gly Lys Glu Ile Ala Arg Asp Gln Val Thr
        675                 680                 685

Thr Ala Gly Ala Pro Ala Ala Val Lys Leu Thr Ala Asp Arg Lys Val
        690                 695                 700

Ile Lys Ala Asp Gly Thr Asp Leu Ser Phe Ile Thr Ala Glu Ile Val
705                 710                 715                 720

Asp Ser Lys Gly Asn Val Val Pro Asn Ala Asp His Leu Ile Gln Phe
            725                 730                 735

His Leu Ser Gly His Gly Glu Leu Ala Gly Val Asp Asn Gly Asp Ala
            740                 745                 750

Ala Ser Val Glu Arg Tyr Lys Asp Asn Lys Arg Lys Ala Phe Ser Gly
        755                 760                 765

Lys Ala Leu Ala Ile Val Gln Ser Asn Lys Leu Asp Gly Asn Ile Thr
        770                 775                 780

Leu His Ala Ser Ala Glu Gly Leu Ser Ser Gly Asn Val Thr Ile Phe
785                 790                 795                 800
```

-continued

Thr Thr Ala Ser Ala Asp Gln Asn Ser Ile Thr Ala Gly Ile Asp
             805                 810                 815

Glu Val Asn Val Leu Val Asp Phe Asn Val Pro Glu Leu Pro Ser
         820                 825                 830

Gln Ile Lys Val Tyr Tyr Ser Asp Ser Thr Val Glu Met Lys Pro Val
     835                 840                 845

Thr Trp Asp Ala Val Asp Pro Asn Leu Leu Asn Thr Ala Gly Lys Ile
 850                 855                 860

Ile Val Glu Gly Thr Val Glu Gly Thr Asp Lys Ala Lys Ala Leu
865                 870                 875                 880

Leu Ile Val Lys Gly Asn Gly Gln Glu Asn Ser Glu Tyr Arg Ile Asp
             885                 890                 895

Leu Phe Ser Pro Asp Pro Lys Leu Ile Ser Thr Glu Leu Thr Val Glu
         900                 905                 910

Lys Thr Asn Ile Met Glu Asp Phe Ile Asp Ile Lys Val Ile Gly
     915                 920                 925

Gln Leu Glu Asn Lys Glu Val Val Asp Leu Ser Asn Phe Met Pro Ile
 930                 935                 940

Tyr Glu Phe Asp Cys Asp Ile Ile Lys Ile Glu Gly Asn Lys Leu Tyr
945                 950                 955                 960

Ala Leu Glu Glu Gly Leu Val Lys Val Thr Ala Val Thr Tyr Lys
             965                 970                 975

Gly Arg Thr Val Thr Ser Pro Glu Met Met Leu Lys Ile Thr Lys Asn
         980                 985                 990

Pro Val Pro Lys Thr Ile Thr His Ile Asp Ser Ile Thr Val Val Ala
     995                 1000                1005

Gly Lys Gly Glu Ala Pro Val Leu Pro Ala Thr Ala Val Ala His
         1010                1015                1020

Phe Asp Arg Gly Met Pro Arg Asp Val Lys Val Lys Trp Glu Ile
 1025                1030                1035

Val Asn Pro Ala Leu Tyr Gln Asn Leu Gly Glu Phe Thr Val Ser
     1040                1045                1050

Gly Asp Val Glu Gly Thr
         1055

<210> SEQ ID NO 15
<211> LENGTH: 41
<212> TYPE: DNA
<213> ORGANISM: Artificial Sequence
<220> FEATURE:
<223> OTHER INFORMATION: BgaII-1059-D92-R

<400> SEQUENCE: 15
gcgaccggcg ctcagctgtt atgtcccttc gacatcacct g        41

<210> SEQ ID NO 16
<211> LENGTH: 1066
<212> TYPE: PRT
<213> ORGANISM: Artificial Sequence
<220> FEATURE:
<223> OTHER INFORMATION: BgaII-1066

<400> SEQUENCE: 16

Met Arg Arg Ile Asn Phe Asn Asp Asn Trp Arg Phe Gln Arg Glu Ile
1               5                   10                  15

Ser Thr Ser Leu Arg Glu Ala Gln Lys Pro Ser Phe Asn Asp His Ser
             20                  25                  30

```
Trp Arg Gln Leu Ser Leu Pro His Asp Trp Ser Ile Glu Leu Asp Phe
         35                  40                  45

Asn Lys Asp Ser Leu Ala Thr His Glu Gly Gly Tyr Leu Asp Gly Gly
 50                  55                  60

Val Gly Trp Tyr Arg Lys Thr Phe Thr Val Pro Ser Ala Met Glu Gly
 65                  70                  75                  80

Lys Arg Ile Ser Leu Asp Phe Asp Gly Val Tyr Met Asn Ser Thr Thr
                 85                  90                  95

Tyr Leu Asn Gly Glu Glu Leu Gly Thr Tyr Pro Phe Gly Tyr Asn Ala
             100                 105                 110

Phe Ser Tyr Asp Ile Thr Asp Lys Leu Phe Met Asp Gly Arg Glu Asn
             115                 120                 125

Val Leu Ala Val Lys Val Asp Asn Thr Gln Pro Ser Ser Arg Trp Tyr
         130                 135                 140

Ser Gly Ser Gly Ile Tyr Arg Asn Val Tyr Leu Thr Val Thr Asn Pro
145                 150                 155                 160

Val His Val Ala Arg Tyr Gly Thr Phe Val Thr Thr Pro Asp Leu Glu
                 165                 170                 175

Ser Ala Tyr Ala Ala Arg Lys Ala Glu Val Asn Ile Lys Thr Lys Ile
             180                 185                 190

Asn Asn Asp Ser Asp Ala Ala Val Gln Val Lys Val Lys Ser Thr Ile
         195                 200                 205

Tyr Asp Thr Asp Gly Lys Glu Val Ala Ser Val Val Ser Gln Glu Lys
         210                 215                 220

Thr Ala Ala Ala Gly Thr Thr Ala His Phe Glu Asp Asn Thr Val Ile
225                 230                 235                 240

Glu Asn Pro Glu Leu Trp Ser Leu Asp Asn Pro Tyr Arg Tyr Lys Leu
                 245                 250                 255

Val Thr Asp Val Leu Ile Gly Gly Glu Thr Val Asp Thr Tyr Glu Thr
             260                 265                 270

Arg Phe Gly Ala Arg Phe Phe Lys Phe Asp Ala Asn Glu Gly Phe Ser
         275                 280                 285

Leu Asn Gly Lys Pro Met Lys Leu Tyr Gly Val Ser Met His His Asp
290                 295                 300

Leu Gly Ala Leu Gly Ala Ala Thr Asn Ala Arg Ala Val Glu Arg Gln
305                 310                 315                 320

Leu Gln Ile Met Lys Asp Met Gly Val Asn Ala Ile Arg Gly Thr His
                 325                 330                 335

Asn Pro Val Ser Pro Glu Phe Leu Glu Ala Val Asn Asn Leu Gly Leu
             340                 345                 350

Leu Leu Ile Glu Glu Ala Phe Asp Cys Trp Ser Gln Ser Lys Lys Thr
         355                 360                 365

Tyr Asp Tyr Gly Arg Phe Phe Thr Arg Trp Ala Glu His Asp Val Lys
         370                 375                 380

Glu Met Val Asp Arg Gly Lys Asn Glu Pro Ser Ile Ile Met Trp Ser
385                 390                 395                 400

Ile Gly Asn Glu Ile Tyr Asp Thr Thr Ser Pro Ser Gly Val Glu Thr
                 405                 410                 415

Ala Arg Asn Leu Val Arg Trp Ile Lys Glu Ile Asp Thr Thr Arg Pro
             420                 425                 430

Thr Thr Ile Gly Glu Asp Lys Thr Arg Gly Asp Lys Val Asn Val Thr
         435                 440                 445

Pro Ile Asp Pro Asn Ile Leu Glu Ile Phe His Thr Val Asp Val Val
```

```
            450                 455                 460
Gly Leu Asn Tyr Ser Glu Asn Tyr Val Gly Tyr His Glu Gln His
465                 470                 475                 480

Pro Asn Trp Lys Leu Tyr Gly Ser Glu Thr Ser Ala Thr Arg Ser
                485                 490                 495

Arg Gly Val Tyr Thr His Pro Tyr Glu Tyr Asn Leu Gly Thr Lys Tyr
                500                 505                 510

Asp Asp Leu Gln Gln Ser Ser Tyr Asp Asn Asp Tyr Val Pro Trp Gly
                515                 520                 525

Arg Thr Ala Glu Asp Ala Trp Lys Ser Asp Arg Asp Leu Lys His Phe
            530                 535                 540

Ala Gly Gln Phe Ile Trp Thr Gly Phe Asp Tyr Ile Gly Glu Pro Thr
545                 550                 555                 560

Pro Tyr Tyr Asp Ser Tyr Pro Ala Lys Ser Ser Tyr Phe Gly Ala Val
                565                 570                 575

Asp Thr Ala Gly Phe Pro Lys Asp Ile Phe Tyr Tyr Gln Ser Gln
                580                 585                 590

Trp Lys Lys Glu Pro Met Val His Leu Leu Pro His Trp Asn Trp Thr
            595                 600                 605

Glu Gly Glu Pro Val Arg Val Leu Ala Tyr Thr Asn Ala His Gln Val
610                 615                 620

Glu Leu Phe Leu Asn Gly Lys Ser Leu Gly Val Arg Gly Tyr Glu Asn
625                 630                 635                 640

Lys Lys Thr Ser Trp Gly Ala Pro Tyr Lys Glu Thr Lys Asp Gly Lys
                645                 650                 655

Thr Tyr Leu Glu Trp Ala Val Pro Phe Lys Ala Gly Thr Leu Glu Ala
                660                 665                 670

Val Ala Met Asp Glu Asn Gly Lys Glu Ile Ala Arg Asp Gln Val Thr
            675                 680                 685

Thr Ala Gly Ala Pro Ala Ala Val Lys Leu Thr Ala Asp Arg Lys Val
            690                 695                 700

Ile Lys Ala Asp Gly Thr Asp Leu Ser Phe Ile Thr Ala Glu Ile Val
705                 710                 715                 720

Asp Ser Lys Gly Asn Val Val Pro Asn Ala Asp His Leu Ile Gln Phe
                725                 730                 735

His Leu Ser Gly His Gly Glu Leu Ala Gly Val Asp Asn Gly Asp Ala
                740                 745                 750

Ala Ser Val Glu Arg Tyr Lys Asp Asn Lys Arg Lys Ala Phe Ser Gly
                755                 760                 765

Lys Ala Leu Ala Ile Val Gln Ser Asn Lys Leu Asp Gly Asn Ile Thr
            770                 775                 780

Leu His Ala Ser Ala Glu Gly Leu Ser Ser Gly Asn Val Thr Ile Phe
785                 790                 795                 800

Thr Thr Ala Ser Ala Asp Gln Asn Ser Ile Thr Ile Ala Gly Ile Asp
                805                 810                 815

Glu Val Asn Val Leu Val Asp Phe Asn Val Val Pro Glu Leu Pro Ser
                820                 825                 830

Gln Ile Lys Val Tyr Tyr Ser Asp Ser Thr Val Glu Met Lys Pro Val
            835                 840                 845

Thr Trp Asp Ala Val Asp Pro Asn Leu Leu Asn Thr Ala Gly Lys Ile
            850                 855                 860

Ile Val Glu Gly Thr Val Glu Gly Thr Asp Lys Lys Ala Lys Ala Leu
865                 870                 875                 880
```

```
Leu Ile Val Lys Gly Asn Gly Gln Glu Asn Ser Glu Tyr Arg Ile Asp
            885                 890                 895

Leu Phe Ser Pro Asp Pro Lys Leu Ile Ser Thr Glu Leu Thr Val Glu
        900                 905                 910

Lys Thr Asn Ile Met Glu Asp Asp Phe Ile Asp Ile Lys Val Ile Gly
            915                 920                 925

Gln Leu Glu Asn Lys Glu Val Val Asp Leu Ser Asn Phe Met Pro Ile
        930                 935                 940

Tyr Glu Phe Asp Cys Asp Ile Ile Lys Ile Glu Gly Asn Lys Leu Tyr
945                 950                 955                 960

Ala Leu Glu Glu Gly Leu Val Lys Val Thr Ala Ala Val Thr Tyr Lys
                965                 970                 975

Gly Arg Thr Val Thr Ser Pro Glu Met Met Leu Lys Ile Thr Lys Asn
            980                 985                 990

Pro Val Pro Lys Thr Ile Thr His Ile Asp Ser Ile Thr Val Val Ala
        995                 1000                1005

Gly Lys Gly Glu Ala Pro Val Leu Pro Ala Thr Ala Val Ala His
    1010                1015                1020

Phe Asp Arg Gly Met Pro Arg Asp Val Lys Val Lys Trp Glu Ile
    1025                1030                1035

Val Asn Pro Ala Leu Tyr Gln Asn Leu Gly Glu Phe Thr Val Ser
    1040                1045                1050

Gly Asp Val Glu Gly Thr Glu Ile Lys Ala Gln Ala Lys
    1055                1060                1065

<210> SEQ ID NO 17
<211> LENGTH: 41
<212> TYPE: DNA
<213> ORGANISM: Artificial Sequence
<220> FEATURE:
<223> OTHER INFORMATION: BgaII-1066-D92-R

<400> SEQUENCE: 17
gcgaccggcg ctcagctgtt actttgcctg ggccttgatt t                        41

<210> SEQ ID NO 18
<211> LENGTH: 1115
<212> TYPE: PRT
<213> ORGANISM: Artificial Sequence
<220> FEATURE:
<223> OTHER INFORMATION: BgaII-1115

<400> SEQUENCE: 18

Met Arg Arg Ile Asn Phe Asn Asp Asn Trp Arg Phe Gln Arg Glu Ile
1               5                   10                  15

Ser Thr Ser Leu Arg Glu Ala Gln Lys Pro Ser Phe Asn Asp His Ser
            20                  25                  30

Trp Arg Gln Leu Ser Leu Pro His Asp Trp Ser Ile Glu Leu Asp Phe
        35                  40                  45

Asn Lys Asp Ser Leu Ala Thr His Glu Gly Gly Tyr Leu Asp Gly Gly
    50                  55                  60

Val Gly Trp Tyr Arg Lys Thr Phe Thr Val Pro Ser Ala Met Glu Gly
65                  70                  75                  80

Lys Arg Ile Ser Leu Asp Phe Asp Gly Val Tyr Met Asn Ser Thr Thr
                85                  90                  95

Tyr Leu Asn Gly Glu Glu Leu Gly Thr Tyr Pro Phe Gly Tyr Asn Ala
            100                 105                 110
```

```
Phe Ser Tyr Asp Ile Thr Asp Lys Leu Phe Met Asp Gly Arg Glu Asn
            115                 120                 125

Val Leu Ala Val Lys Val Asp Asn Thr Gln Pro Ser Ser Arg Trp Tyr
130                 135                 140

Ser Gly Ser Gly Ile Tyr Arg Asn Val Tyr Leu Thr Val Thr Asn Pro
145                 150                 155                 160

Val His Val Ala Arg Tyr Gly Thr Phe Val Thr Thr Pro Asp Leu Glu
                165                 170                 175

Ser Ala Tyr Ala Ala Arg Lys Ala Glu Val Asn Ile Lys Thr Lys Ile
                180                 185                 190

Asn Asn Asp Ser Asp Ala Ala Val Gln Val Lys Val Lys Ser Thr Ile
            195                 200                 205

Tyr Asp Thr Asp Gly Lys Glu Val Ala Ser Val Val Ser Gln Glu Lys
210                 215                 220

Thr Ala Ala Gly Thr Thr Ala His Phe Glu Asp Asn Thr Val Ile
225                 230                 235                 240

Glu Asn Pro Glu Leu Trp Ser Leu Asp Asn Pro Tyr Arg Tyr Lys Leu
                245                 250                 255

Val Thr Asp Val Leu Ile Gly Gly Glu Thr Val Asp Thr Tyr Glu Thr
                260                 265                 270

Arg Phe Gly Ala Arg Phe Phe Lys Phe Asp Ala Asn Glu Gly Phe Ser
            275                 280                 285

Leu Asn Gly Lys Pro Met Lys Leu Tyr Gly Val Ser Met His His Asp
            290                 295                 300

Leu Gly Ala Leu Gly Ala Ala Thr Asn Ala Arg Ala Val Glu Arg Gln
305                 310                 315                 320

Leu Gln Ile Met Lys Asp Met Gly Val Asn Ala Ile Arg Gly Thr His
                325                 330                 335

Asn Pro Val Ser Pro Glu Phe Leu Glu Ala Val Asn Asn Leu Gly Leu
            340                 345                 350

Leu Leu Ile Glu Glu Ala Phe Asp Cys Trp Ser Gln Ser Lys Lys Thr
            355                 360                 365

Tyr Asp Tyr Gly Arg Phe Phe Thr Arg Trp Ala Glu His Asp Val Lys
            370                 375                 380

Glu Met Val Asp Arg Gly Lys Asn Glu Pro Ser Ile Ile Met Trp Ser
385                 390                 395                 400

Ile Gly Asn Glu Ile Tyr Asp Thr Thr Ser Pro Ser Gly Val Glu Thr
                405                 410                 415

Ala Arg Asn Leu Val Arg Trp Ile Lys Glu Ile Asp Thr Thr Arg Pro
            420                 425                 430

Thr Thr Ile Gly Glu Asp Lys Thr Arg Gly Asp Lys Val Asn Val Thr
            435                 440                 445

Pro Ile Asp Pro Asn Ile Leu Glu Ile Phe His Thr Val Asp Val Val
450                 455                 460

Gly Leu Asn Tyr Ser Glu Asn Asn Tyr Val Gly Tyr His Glu Gln His
465                 470                 475                 480

Pro Asn Trp Lys Leu Tyr Gly Ser Glu Thr Ser Ser Ala Thr Arg Ser
                485                 490                 495

Arg Gly Val Tyr Thr His Pro Tyr Glu Tyr Asn Leu Gly Thr Lys Tyr
                500                 505                 510

Asp Asp Leu Gln Gln Ser Ser Tyr Asp Asn Asp Tyr Val Pro Trp Gly
            515                 520                 525
```

-continued

```
Arg Thr Ala Glu Asp Ala Trp Lys Ser Asp Arg Asp Leu Lys His Phe
530                 535                 540

Ala Gly Gln Phe Ile Trp Thr Gly Phe Asp Tyr Ile Gly Glu Pro Thr
545                 550                 555                 560

Pro Tyr Tyr Asp Ser Tyr Pro Ala Lys Ser Ser Tyr Phe Gly Ala Val
                565                 570                 575

Asp Thr Ala Gly Phe Pro Lys Asp Ile Phe Tyr Tyr Gln Ser Gln
                580                 585                 590

Trp Lys Lys Glu Pro Met Val His Leu Leu Pro His Trp Asn Trp Thr
        595                 600                 605

Glu Gly Glu Pro Val Arg Val Leu Ala Tyr Thr Asn Ala His Gln Val
610                 615                 620

Glu Leu Phe Leu Asn Gly Lys Ser Leu Gly Val Arg Gly Tyr Glu Asn
625                 630                 635                 640

Lys Lys Thr Ser Trp Gly Ala Pro Tyr Lys Glu Thr Lys Asp Gly Lys
                645                 650                 655

Thr Tyr Leu Glu Trp Ala Val Pro Phe Lys Ala Gly Thr Leu Glu Ala
                660                 665                 670

Val Ala Met Asp Glu Asn Gly Lys Glu Ile Ala Arg Asp Gln Val Thr
                675                 680                 685

Thr Ala Gly Ala Pro Ala Ala Val Lys Leu Thr Ala Asp Arg Lys Val
690                 695                 700

Ile Lys Ala Asp Gly Thr Asp Leu Ser Phe Ile Thr Ala Glu Ile Val
705                 710                 715                 720

Asp Ser Lys Gly Asn Val Val Pro Asn Ala Asp His Leu Ile Gln Phe
                725                 730                 735

His Leu Ser Gly His Gly Glu Leu Ala Gly Val Asp Asn Gly Asp Ala
                740                 745                 750

Ala Ser Val Glu Arg Tyr Lys Asp Asn Lys Arg Lys Ala Phe Ser Gly
                755                 760                 765

Lys Ala Leu Ala Ile Val Gln Ser Asn Lys Leu Asp Gly Asn Ile Thr
770                 775                 780

Leu His Ala Ser Ala Glu Gly Leu Ser Ser Gly Asn Val Thr Ile Phe
785                 790                 795                 800

Thr Thr Ala Ser Ala Asp Gln Asn Ser Ile Thr Ile Ala Gly Ile Asp
                805                 810                 815

Glu Val Asn Val Leu Val Asp Phe Asn Val Val Pro Glu Leu Pro Ser
                820                 825                 830

Gln Ile Lys Val Tyr Tyr Ser Asp Ser Thr Val Glu Met Lys Pro Val
                835                 840                 845

Thr Trp Asp Ala Val Asp Pro Asn Leu Leu Asn Thr Ala Gly Lys Ile
850                 855                 860

Ile Val Glu Gly Thr Val Gly Thr Asp Lys Lys Ala Lys Ala Leu
865                 870                 875                 880

Leu Ile Val Lys Gly Asn Gly Gln Glu Asn Ser Glu Tyr Arg Ile Asp
                885                 890                 895

Leu Phe Ser Pro Asp Pro Lys Leu Ile Ser Thr Glu Leu Thr Val Glu
                900                 905                 910

Lys Thr Asn Ile Met Glu Asp Asp Phe Ile Asp Ile Lys Val Ile Gly
                915                 920                 925

Gln Leu Glu Asn Lys Val Val Asp Leu Ser Asn Phe Met Pro Ile
930                 935                 940

Tyr Glu Phe Asp Cys Asp Ile Ile Lys Ile Glu Gly Asn Lys Leu Tyr
```

```
                    945                 950                 955                 960
Ala Leu Glu Glu Gly Leu Val Lys Val Thr Ala Ala Val Thr Tyr Lys
                965                 970                 975

Gly Arg Thr Val Thr Ser Pro Glu Met Met Leu Lys Ile Thr Lys Asn
                980                 985                 990

Pro Val Pro Lys Thr Ile Thr His Ile Asp Ser Ile Thr Val Val Ala
                995                1000                1005

Gly Lys Gly Glu Ala Pro Val Leu Pro Ala Thr Ala Val Ala His
            1010                1015                1020

Phe Asp Arg Gly Met Pro Arg Asp Val Lys Val Lys Trp Glu Ile
            1025                1030                1035

Val Asn Pro Ala Leu Tyr Gln Asn Leu Gly Glu Phe Thr Val Ser
            1040                1045                1050

Gly Asp Val Glu Gly Thr Glu Ile Lys Ala Gln Ala Lys Val Met
            1055                1060                1065

Val Arg Ser Ala Leu Ala Ile Glu Thr Ile Ser Met Ala Val Leu
            1070                1075                1080

Pro Asn Gln Lys Pro Glu Leu Pro Gln Lys Val Thr Val Tyr Tyr
            1085                1090                1095

Ser Asp Gly Thr Glu Glu Gln Ala Asp Val Asp Trp Asp Ala Met
            1100                1105                1110

Pro Ser
    1115
```

<210> SEQ ID NO 19
<211> LENGTH: 41
<212> TYPE: DNA
<213> ORGANISM: Artificial Sequence
<220> FEATURE:
<223> OTHER INFORMATION: BgaII-1115-D92-R

<400> SEQUENCE: 19
gcgaccggcg ctcagctgtt atgatggcat agcgtcccaa t                         41

<210> SEQ ID NO 20
<211> LENGTH: 1164
<212> TYPE: PRT
<213> ORGANISM: Artificial Sequence
<220> FEATURE:
<223> OTHER INFORMATION: BgaII-1164

<400> SEQUENCE: 20

```
Met Arg Arg Ile Asn Phe Asn Asp Asn Trp Arg Phe Gln Arg Glu Ile
1               5                  10                  15

Ser Thr Ser Leu Arg Glu Ala Gln Lys Pro Ser Phe Asn Asp His Ser
                20                  25                  30

Trp Arg Gln Leu Ser Leu Pro His Asp Trp Ser Ile Glu Leu Asp Phe
            35                  40                  45

Asn Lys Asp Ser Leu Ala Thr His Glu Gly Gly Tyr Leu Asp Gly Gly
        50                  55                  60

Val Gly Trp Tyr Arg Lys Thr Phe Thr Val Pro Ser Ala Met Glu Gly
65                  70                  75                  80

Lys Arg Ile Ser Leu Asp Phe Asp Gly Val Tyr Met Asn Ser Thr Thr
                85                  90                  95

Tyr Leu Asn Gly Glu Glu Leu Gly Thr Tyr Pro Phe Gly Tyr Asn Ala
                100                 105                 110

Phe Ser Tyr Asp Ile Thr Asp Lys Leu Phe Met Asp Gly Arg Glu Asn
```

-continued

```
            115                 120                 125
Val Leu Ala Val Lys Val Asp Asn Thr Gln Pro Ser Ser Arg Trp Tyr
130                 135                 140
Ser Gly Ser Gly Ile Tyr Arg Asn Val Tyr Leu Thr Val Thr Asn Pro
145                 150                 155                 160
Val His Val Ala Arg Tyr Gly Thr Phe Val Thr Thr Pro Asp Leu Glu
                    165                 170                 175
Ser Ala Tyr Ala Ala Arg Lys Ala Glu Val Asn Ile Lys Thr Lys Ile
                    180                 185                 190
Asn Asn Asp Ser Asp Ala Ala Val Gln Val Lys Val Lys Ser Thr Ile
                    195                 200                 205
Tyr Asp Thr Asp Gly Lys Glu Val Ala Ser Val Val Ser Gln Glu Lys
210                 215                 220
Thr Ala Ala Ala Gly Thr Thr Ala His Phe Glu Asp Asn Thr Val Ile
225                 230                 235                 240
Glu Asn Pro Glu Leu Trp Ser Leu Asp Asn Pro Tyr Arg Tyr Lys Leu
                    245                 250                 255
Val Thr Asp Val Leu Ile Gly Gly Glu Thr Val Asp Thr Tyr Glu Thr
                260                 265                 270
Arg Phe Gly Ala Arg Phe Phe Lys Phe Asp Ala Asn Glu Gly Phe Ser
                275                 280                 285
Leu Asn Gly Lys Pro Met Lys Leu Tyr Gly Val Ser Met His His Asp
290                 295                 300
Leu Gly Ala Leu Gly Ala Ala Thr Asn Ala Arg Ala Val Glu Arg Gln
305                 310                 315                 320
Leu Gln Ile Met Lys Asp Met Gly Val Asn Ala Ile Arg Gly Thr His
                    325                 330                 335
Asn Pro Val Ser Pro Glu Phe Leu Glu Ala Val Asn Asn Leu Gly Leu
                340                 345                 350
Leu Leu Ile Glu Glu Ala Phe Asp Cys Trp Ser Gln Ser Lys Lys Thr
                355                 360                 365
Tyr Asp Tyr Gly Arg Phe Phe Thr Arg Trp Ala Glu His Asp Val Lys
370                 375                 380
Glu Met Val Asp Arg Gly Lys Asn Glu Pro Ser Ile Ile Met Trp Ser
385                 390                 395                 400
Ile Gly Asn Glu Ile Tyr Asp Thr Thr Ser Pro Ser Gly Val Glu Thr
                    405                 410                 415
Ala Arg Asn Leu Val Arg Trp Ile Lys Glu Ile Asp Thr Thr Arg Pro
                420                 425                 430
Thr Thr Ile Gly Glu Asp Lys Thr Arg Gly Asp Lys Val Asn Val Thr
                435                 440                 445
Pro Ile Asp Pro Asn Ile Leu Glu Ile Phe His Thr Val Asp Val Val
                450                 455                 460
Gly Leu Asn Tyr Ser Glu Asn Asn Tyr Val Gly Tyr His Glu Gln His
465                 470                 475                 480
Pro Asn Trp Lys Leu Tyr Gly Ser Glu Thr Ser Ser Ala Thr Arg Ser
                    485                 490                 495
Arg Gly Val Tyr Thr His Pro Tyr Glu Tyr Asn Leu Gly Thr Lys Tyr
                500                 505                 510
Asp Asp Leu Gln Gln Ser Ser Tyr Asp Asn Asp Tyr Val Pro Trp Gly
                515                 520                 525
Arg Thr Ala Glu Asp Ala Trp Lys Ser Asp Arg Asp Leu Lys His Phe
530                 535                 540
```

-continued

```
Ala Gly Gln Phe Ile Trp Thr Gly Phe Asp Tyr Ile Gly Glu Pro Thr
545                 550                 555                 560

Pro Tyr Tyr Asp Ser Tyr Pro Ala Lys Ser Ser Tyr Phe Gly Ala Val
                565                 570                 575

Asp Thr Ala Gly Phe Pro Lys Asp Ile Phe Tyr Tyr Gln Ser Gln
            580                 585                 590

Trp Lys Lys Glu Pro Met Val His Leu Leu Pro His Trp Asn Trp Thr
        595                 600                 605

Glu Gly Glu Pro Val Arg Val Leu Ala Tyr Thr Asn Ala His Gln Val
610                 615                 620

Glu Leu Phe Leu Asn Gly Lys Ser Leu Gly Val Arg Gly Tyr Glu Asn
625                 630                 635                 640

Lys Lys Thr Ser Trp Gly Ala Pro Tyr Lys Glu Thr Lys Asp Gly Lys
                645                 650                 655

Thr Tyr Leu Glu Trp Ala Val Pro Phe Lys Ala Gly Thr Leu Glu Ala
            660                 665                 670

Val Ala Met Asp Glu Asn Gly Lys Glu Ile Ala Arg Asp Gln Val Thr
        675                 680                 685

Thr Ala Gly Ala Pro Ala Ala Val Lys Leu Thr Ala Asp Arg Lys Val
    690                 695                 700

Ile Lys Ala Asp Gly Thr Asp Leu Ser Phe Ile Thr Ala Glu Ile Val
705                 710                 715                 720

Asp Ser Lys Gly Asn Val Val Pro Asn Ala Asp His Leu Ile Gln Phe
                725                 730                 735

His Leu Ser Gly His Gly Glu Leu Ala Gly Val Asp Asn Gly Asp Ala
            740                 745                 750

Ala Ser Val Glu Arg Tyr Lys Asp Asn Lys Arg Lys Ala Phe Ser Gly
        755                 760                 765

Lys Ala Leu Ala Ile Val Gln Ser Asn Lys Leu Asp Gly Asn Ile Thr
    770                 775                 780

Leu His Ala Ser Ala Glu Gly Leu Ser Ser Gly Asn Val Thr Ile Phe
785                 790                 795                 800

Thr Thr Ala Ser Ala Asp Gln Asn Ser Ile Thr Ile Ala Gly Ile Asp
                805                 810                 815

Glu Val Asn Val Leu Val Asp Phe Asn Val Val Pro Glu Leu Pro Ser
            820                 825                 830

Gln Ile Lys Val Tyr Tyr Ser Asp Ser Thr Val Glu Met Lys Pro Val
        835                 840                 845

Thr Trp Asp Ala Val Asp Pro Asn Leu Leu Asn Thr Ala Gly Lys Ile
    850                 855                 860

Ile Val Glu Gly Thr Val Glu Gly Thr Asp Lys Lys Ala Lys Ala Leu
865                 870                 875                 880

Leu Ile Val Lys Gly Asn Gly Gln Glu Asn Ser Glu Tyr Arg Ile Asp
                885                 890                 895

Leu Phe Ser Pro Asp Pro Lys Leu Ile Ser Thr Glu Leu Thr Val Glu
            900                 905                 910

Lys Thr Asn Ile Met Glu Asp Asp Phe Ile Asp Ile Lys Val Ile Gly
        915                 920                 925

Gln Leu Glu Asn Lys Glu Val Val Asp Leu Ser Asn Phe Met Pro Ile
    930                 935                 940

Tyr Glu Phe Asp Cys Asp Ile Ile Lys Ile Glu Gly Asn Lys Leu Tyr
945                 950                 955                 960
```

Ala Leu Glu Glu Gly Leu Val Lys Val Thr Ala Val Thr Tyr Lys
            965                 970                 975

Gly Arg Thr Val Thr Ser Pro Glu Met Met Leu Lys Ile Thr Lys Asn
        980                 985                 990

Pro Val Pro Lys Thr Ile Thr His Ile Asp Ser Ile Thr Val Val Ala
    995                 1000                1005

Gly Lys Gly Glu Ala Pro Val Leu Pro Ala Thr Ala Val Ala His
    1010                1015                1020

Phe Asp Arg Gly Met Pro Arg Asp Val Lys Val Lys Trp Glu Ile
    1025                1030                1035

Val Asn Pro Ala Leu Tyr Gln Asn Leu Gly Glu Phe Thr Val Ser
    1040                1045                1050

Gly Asp Val Glu Gly Thr Glu Ile Lys Ala Gln Ala Lys Val Met
    1055                1060                1065

Val Arg Ser Ala Leu Ala Ile Glu Thr Ile Ser Met Ala Val Leu
    1070                1075                1080

Pro Asn Gln Lys Pro Glu Leu Pro Gln Leu Val Thr Val Tyr Tyr
    1085                1090                1095

Ser Asp Gly Thr Glu Glu Gln Ala Asp Val Asp Trp Asp Ala Met
    1100                1105                1110

Pro Ser Ala Glu Leu Lys Ser Glu Gly Val Val Lys Val Lys Gly
    1115                1120                1125

Ser Val Lys Gly Val Asp Leu Lys Ala Thr Ala Gln Ile Arg Val
    1130                1135                1140

Thr Ser Glu Val Gly Gly Val Gln Asn Ile Ser Arg Ala Lys Asn
    1145                1150                1155

Gly Tyr Glu Tyr Pro Lys
    1160

<210> SEQ ID NO 21
<211> LENGTH: 42
<212> TYPE: DNA
<213> ORGANISM: Artificial Sequence
<220> FEATURE:
<223> OTHER INFORMATION: BgaII-1164-D92-R

<400> SEQUENCE: 21
aatggctacg aatatccgaa ataacagctg agcgccggtc gc                42

<210> SEQ ID NO 22
<211> LENGTH: 1200
<212> TYPE: PRT
<213> ORGANISM: Artificial Sequence
<220> FEATURE:
<223> OTHER INFORMATION: BgaII-1200

<400> SEQUENCE: 22

Met Arg Arg Ile Asn Phe Asn Asp Asn Trp Arg Phe Gln Arg Glu Ile
1               5                   10                  15

Ser Thr Ser Leu Arg Glu Ala Gln Lys Pro Ser Phe Asn Asp His Ser
            20                  25                  30

Trp Arg Gln Leu Ser Leu Pro His Asp Trp Ser Ile Glu Leu Asp Phe
        35                  40                  45

Asn Lys Asp Ser Leu Ala Thr His Glu Gly Gly Tyr Leu Asp Gly Gly
    50                  55                  60

Val Gly Trp Tyr Arg Lys Thr Phe Thr Val Pro Ser Ala Met Glu Gly
65                  70                  75                  80

Lys Arg Ile Ser Leu Asp Phe Asp Gly Val Tyr Met Asn Ser Thr Thr
                85                  90                  95

Tyr Leu Asn Gly Glu Glu Leu Gly Thr Tyr Pro Phe Gly Tyr Asn Ala
            100                 105                 110

Phe Ser Tyr Asp Ile Thr Asp Lys Leu Phe Met Asp Gly Arg Glu Asn
            115                 120                 125

Val Leu Ala Val Lys Val Asp Asn Thr Gln Pro Ser Ser Arg Trp Tyr
            130                 135                 140

Ser Gly Ser Gly Ile Tyr Arg Asn Val Tyr Leu Thr Val Thr Asn Pro
145                 150                 155                 160

Val His Val Ala Arg Tyr Gly Thr Phe Val Thr Thr Pro Asp Leu Glu
                165                 170                 175

Ser Ala Tyr Ala Ala Arg Lys Ala Glu Val Asn Ile Lys Thr Lys Ile
                180                 185                 190

Asn Asn Asp Ser Asp Ala Ala Val Gln Val Lys Val Lys Ser Thr Ile
            195                 200                 205

Tyr Asp Thr Asp Gly Lys Glu Val Ala Ser Val Ser Gln Glu Lys
            210                 215                 220

Thr Ala Ala Gly Thr Thr Ala His Phe Glu Asp Asn Thr Val Ile
225                 230                 235                 240

Glu Asn Pro Glu Leu Trp Ser Leu Asp Asn Pro Tyr Arg Tyr Lys Leu
                245                 250                 255

Val Thr Asp Val Leu Ile Gly Gly Glu Thr Val Asp Thr Tyr Glu Thr
            260                 265                 270

Arg Phe Gly Ala Arg Phe Phe Lys Phe Asp Ala Asn Glu Gly Phe Ser
            275                 280                 285

Leu Asn Gly Lys Pro Met Lys Leu Tyr Gly Val Ser Met His His Asp
            290                 295                 300

Leu Gly Ala Leu Gly Ala Ala Thr Asn Ala Arg Ala Val Glu Arg Gln
305                 310                 315                 320

Leu Gln Ile Met Lys Asp Met Gly Val Asn Ala Ile Arg Gly Thr His
                325                 330                 335

Asn Pro Val Ser Pro Glu Phe Leu Glu Ala Val Asn Asn Leu Gly Leu
            340                 345                 350

Leu Leu Ile Glu Glu Ala Phe Asp Cys Trp Ser Gln Ser Lys Lys Thr
            355                 360                 365

Tyr Asp Tyr Gly Arg Phe Phe Thr Arg Trp Ala Glu His Asp Val Lys
            370                 375                 380

Glu Met Val Asp Arg Gly Lys Asn Glu Pro Ser Ile Ile Met Trp Ser
385                 390                 395                 400

Ile Gly Asn Glu Ile Tyr Asp Thr Thr Ser Pro Ser Gly Val Glu Thr
            405                 410                 415

Ala Arg Asn Leu Val Arg Trp Ile Lys Glu Ile Asp Thr Thr Arg Pro
            420                 425                 430

Thr Thr Ile Gly Glu Asp Lys Thr Arg Gly Asp Lys Val Asn Val Thr
            435                 440                 445

Pro Ile Asp Pro Asn Ile Leu Glu Ile Phe His Thr Val Asp Val Val
            450                 455                 460

Gly Leu Asn Tyr Ser Glu Asn Asn Tyr Val Gly Tyr His Glu Gln His
465                 470                 475                 480

Pro Asn Trp Lys Leu Tyr Gly Ser Glu Thr Ser Ser Ala Thr Arg Ser
                485                 490                 495

Arg Gly Val Tyr Thr His Pro Tyr Glu Tyr Asn Leu Gly Thr Lys Tyr

-continued

```
                500                 505                 510
Asp Asp Leu Gln Gln Ser Ser Tyr Asp Asn Asp Tyr Val Pro Trp Gly
            515                 520                 525
Arg Thr Ala Glu Asp Ala Trp Lys Ser Asp Arg Asp Leu Lys His Phe
        530                 535                 540
Ala Gly Gln Phe Ile Trp Thr Gly Phe Asp Tyr Ile Gly Glu Pro Thr
545                 550                 555                 560
Pro Tyr Tyr Asp Ser Tyr Pro Ala Lys Ser Ser Tyr Phe Gly Ala Val
                565                 570                 575
Asp Thr Ala Gly Phe Pro Lys Asp Ile Phe Tyr Tyr Gln Ser Gln
            580                 585                 590
Trp Lys Lys Glu Pro Met Val His Leu Leu Pro His Trp Asn Trp Thr
        595                 600                 605
Glu Gly Glu Pro Val Arg Val Leu Ala Tyr Thr Asn Ala His Gln Val
610                 615                 620
Glu Leu Phe Leu Asn Gly Lys Ser Leu Gly Val Arg Gly Tyr Glu Asn
625                 630                 635                 640
Lys Lys Thr Ser Trp Gly Ala Pro Tyr Lys Glu Thr Lys Asp Gly Lys
                645                 650                 655
Thr Tyr Leu Glu Trp Ala Val Pro Phe Lys Ala Gly Thr Leu Glu Ala
            660                 665                 670
Val Ala Met Asp Glu Asn Gly Lys Glu Ile Ala Arg Asp Gln Val Thr
        675                 680                 685
Thr Ala Gly Ala Pro Ala Ala Val Lys Leu Thr Ala Asp Arg Lys Val
        690                 695                 700
Ile Lys Ala Asp Gly Thr Asp Leu Ser Phe Ile Thr Ala Glu Ile Val
705                 710                 715                 720
Asp Ser Lys Gly Asn Val Val Pro Asn Ala Asp His Leu Ile Gln Phe
                725                 730                 735
His Leu Ser Gly His Gly Glu Leu Ala Gly Val Asp Asn Gly Asp Ala
            740                 745                 750
Ala Ser Val Glu Arg Tyr Lys Asp Asn Lys Arg Lys Ala Phe Ser Gly
        755                 760                 765
Lys Ala Leu Ala Ile Val Gln Ser Asn Lys Leu Asp Gly Asn Ile Thr
        770                 775                 780
Leu His Ala Ser Ala Glu Gly Leu Ser Ser Gly Asn Val Thr Ile Phe
785                 790                 795                 800
Thr Thr Ala Ser Ala Asp Gln Asn Ser Ile Thr Ile Ala Gly Ile Asp
                805                 810                 815
Glu Val Asn Val Leu Val Asp Phe Asn Val Val Pro Glu Leu Pro Ser
            820                 825                 830
Gln Ile Lys Val Tyr Tyr Ser Asp Ser Thr Val Glu Met Lys Pro Val
        835                 840                 845
Thr Trp Asp Ala Val Asp Pro Asn Leu Leu Asn Thr Ala Gly Lys Ile
        850                 855                 860
Ile Val Glu Gly Thr Val Gly Thr Asp Lys Lys Ala Lys Ala Leu
865                 870                 875                 880
Leu Ile Val Lys Gly Asn Gly Gln Glu Asn Ser Glu Tyr Arg Ile Asp
                885                 890                 895
Leu Phe Ser Pro Asp Pro Lys Leu Ile Ser Thr Glu Leu Thr Val Glu
            900                 905                 910
Lys Thr Asn Ile Met Glu Asp Asp Phe Ile Asp Ile Lys Val Ile Gly
        915                 920                 925
```

Gln Leu Glu Asn Lys Glu Val Val Asp Leu Ser Asn Phe Met Pro Ile
        930                 935                 940

Tyr Glu Phe Asp Cys Asp Ile Ile Lys Ile Glu Gly Asn Lys Leu Tyr
945                 950                 955                 960

Ala Leu Glu Glu Gly Leu Val Lys Val Thr Ala Ala Val Thr Tyr Lys
                965                 970                 975

Gly Arg Thr Val Thr Ser Pro Glu Met Met Leu Lys Ile Thr Lys Asn
            980                 985                 990

Pro Val Pro Lys Thr Ile Thr His Ile Asp Ser Ile Thr Val Val Ala
        995                 1000                1005

Gly Lys Gly Glu Ala Pro Val Leu Pro Ala Thr Ala Val Ala His
    1010                1015                1020

Phe Asp Arg Gly Met Pro Arg Asp Val Lys Val Lys Trp Glu Ile
    1025                1030                1035

Val Asn Pro Ala Leu Tyr Gln Asn Leu Gly Glu Phe Thr Val Ser
    1040                1045                1050

Gly Asp Val Glu Gly Thr Glu Ile Lys Ala Gln Ala Lys Val Met
    1055                1060                1065

Val Arg Ser Ala Leu Ala Ile Glu Thr Ile Ser Met Ala Val Leu
    1070                1075                1080

Pro Asn Gln Lys Pro Glu Leu Pro Gln Lys Val Thr Val Tyr Tyr
    1085                1090                1095

Ser Asp Gly Thr Glu Glu Gln Ala Asp Val Asp Trp Asp Ala Met
    1100                1105                1110

Pro Ser Ala Glu Leu Lys Ser Glu Gly Val Val Lys Val Lys Gly
    1115                1120                1125

Ser Val Lys Gly Val Asp Leu Lys Ala Thr Ala Gln Ile Arg Val
    1130                1135                1140

Thr Ser Glu Val Gly Gly Val Gln Asn Ile Ser Arg Ala Lys Asn
    1145                1150                1155

Gly Tyr Glu Tyr Pro Lys Ala Glu Ala Ser Phe Thr Asn Thr Gly
    1160                1165                1170

Pro Gly Ser Asn Asp Arg Ile Glu Ala Ile Asn Asp Asp Val Ile
    1175                1180                1185

Ser Tyr Asp Ala Glu Pro His Asn Arg Trp Thr Asn
    1190                1195                1200

<210> SEQ ID NO 23
<211> LENGTH: 41
<212> TYPE: DNA
<213> ORGANISM: Artificial Sequence
<220> FEATURE:
<223> OTHER INFORMATION: BgaII-1200-D92-R

<400> SEQUENCE: 23
gcgaccggcg ctcagctgtt aattcgtcca gcgattatgc g                    41

<210> SEQ ID NO 24
<211> LENGTH: 1302
<212> TYPE: PRT
<213> ORGANISM: Artificial Sequence
<220> FEATURE:
<223> OTHER INFORMATION: BgaII-1302

<400> SEQUENCE: 24

Met Arg Arg Ile Asn Phe Asn Asp Asn Trp Arg Phe Gln Arg Glu Ile
1               5                   10                  15

-continued

Ser Thr Ser Leu Arg Glu Ala Gln Lys Pro Ser Phe Asn Asp His Ser
            20                  25                  30

Trp Arg Gln Leu Ser Leu Pro His Asp Trp Ser Ile Glu Leu Asp Phe
        35                  40                  45

Asn Lys Asp Ser Leu Ala Thr His Glu Gly Gly Tyr Leu Asp Gly Gly
50                  55                  60

Val Gly Trp Tyr Arg Lys Thr Phe Thr Val Pro Ser Ala Met Glu Gly
65                  70                  75                  80

Lys Arg Ile Ser Leu Asp Phe Asp Gly Val Tyr Met Asn Ser Thr Thr
                85                  90                  95

Tyr Leu Asn Gly Glu Glu Leu Gly Thr Tyr Pro Phe Gly Tyr Asn Ala
            100                 105                 110

Phe Ser Tyr Asp Ile Thr Asp Lys Leu Phe Met Asp Gly Arg Glu Asn
        115                 120                 125

Val Leu Ala Val Lys Val Asp Asn Thr Gln Pro Ser Ser Arg Trp Tyr
130                 135                 140

Ser Gly Ser Gly Ile Tyr Arg Asn Val Tyr Leu Thr Val Thr Asn Pro
145                 150                 155                 160

Val His Val Ala Arg Tyr Gly Thr Phe Val Thr Thr Pro Asp Leu Glu
                165                 170                 175

Ser Ala Tyr Ala Ala Arg Lys Ala Glu Val Asn Ile Lys Thr Lys Ile
            180                 185                 190

Asn Asn Asp Ser Asp Ala Ala Val Gln Val Lys Val Lys Ser Thr Ile
        195                 200                 205

Tyr Asp Thr Asp Gly Lys Glu Val Ala Ser Val Val Ser Gln Glu Lys
210                 215                 220

Thr Ala Ala Ala Gly Thr Thr Ala His Phe Glu Asp Asn Thr Val Ile
225                 230                 235                 240

Glu Asn Pro Glu Leu Trp Ser Leu Asp Asn Pro Tyr Arg Tyr Lys Leu
                245                 250                 255

Val Thr Asp Val Leu Ile Gly Gly Glu Thr Val Asp Thr Tyr Glu Thr
            260                 265                 270

Arg Phe Gly Ala Arg Phe Phe Lys Phe Asp Ala Asn Glu Gly Phe Ser
        275                 280                 285

Leu Asn Gly Lys Pro Met Lys Leu Tyr Gly Val Ser Met His His Asp
290                 295                 300

Leu Gly Ala Leu Gly Ala Ala Thr Asn Ala Arg Ala Val Glu Arg Gln
305                 310                 315                 320

Leu Gln Ile Met Lys Asp Met Gly Val Asn Ala Ile Arg Gly Thr His
                325                 330                 335

Asn Pro Val Ser Pro Glu Phe Leu Glu Ala Val Asn Asn Leu Gly Leu
            340                 345                 350

Leu Leu Ile Glu Glu Ala Phe Asp Cys Trp Ser Gln Ser Lys Lys Thr
        355                 360                 365

Tyr Asp Tyr Gly Arg Phe Phe Thr Arg Trp Ala Glu His Asp Val Lys
370                 375                 380

Glu Met Val Asp Arg Gly Lys Asn Glu Pro Ser Ile Ile Met Trp Ser
385                 390                 395                 400

Ile Gly Asn Glu Ile Tyr Asp Thr Thr Ser Pro Ser Gly Val Glu Thr
                405                 410                 415

Ala Arg Asn Leu Val Arg Trp Ile Lys Glu Ile Asp Thr Thr Arg Pro
            420                 425                 430

-continued

```
Thr Thr Ile Gly Glu Asp Lys Thr Arg Gly Asp Lys Val Asn Val Thr
            435                 440                 445

Pro Ile Asp Pro Asn Ile Leu Glu Ile Phe His Thr Val Asp Val Val
450                 455                 460

Gly Leu Asn Tyr Ser Glu Asn Tyr Val Gly Tyr His Glu Gln His
465                 470                 475                 480

Pro Asn Trp Lys Leu Tyr Gly Ser Glu Thr Ser Ala Thr Arg Ser
                485                 490                 495

Arg Gly Val Tyr Thr His Pro Tyr Glu Tyr Asn Leu Gly Thr Lys Tyr
            500                 505                 510

Asp Asp Leu Gln Gln Ser Ser Tyr Asp Asn Asp Tyr Val Pro Trp Gly
            515                 520                 525

Arg Thr Ala Glu Asp Ala Trp Lys Ser Asp Arg Asp Leu Lys His Phe
            530                 535                 540

Ala Gly Gln Phe Ile Trp Thr Gly Phe Asp Tyr Ile Gly Glu Pro Thr
545                 550                 555                 560

Pro Tyr Tyr Asp Ser Tyr Pro Ala Lys Ser Ser Tyr Phe Gly Ala Val
                565                 570                 575

Asp Thr Ala Gly Phe Pro Lys Asp Ile Phe Tyr Tyr Gln Ser Gln
            580                 585                 590

Trp Lys Lys Glu Pro Met Val His Leu Leu Pro His Trp Asn Trp Thr
            595                 600                 605

Glu Gly Glu Pro Val Arg Val Leu Ala Tyr Thr Asn Ala His Gln Val
            610                 615                 620

Glu Leu Phe Leu Asn Gly Lys Ser Leu Gly Val Arg Gly Tyr Glu Asn
625                 630                 635                 640

Lys Lys Thr Ser Trp Gly Ala Pro Tyr Lys Glu Thr Lys Asp Gly Lys
                645                 650                 655

Thr Tyr Leu Glu Trp Ala Val Pro Phe Lys Ala Gly Thr Leu Glu Ala
            660                 665                 670

Val Ala Met Asp Glu Asn Gly Lys Glu Ile Ala Arg Asp Gln Val Thr
            675                 680                 685

Thr Ala Gly Ala Pro Ala Ala Val Lys Leu Thr Ala Asp Arg Lys Val
            690                 695                 700

Ile Lys Ala Asp Gly Thr Asp Leu Ser Phe Ile Thr Ala Glu Ile Val
705                 710                 715                 720

Asp Ser Lys Gly Asn Val Pro Asn Ala Asp His Leu Ile Gln Phe
                725                 730                 735

His Leu Ser Gly His Gly Glu Leu Ala Gly Val Asp Asn Gly Asp Ala
            740                 745                 750

Ala Ser Val Glu Arg Tyr Lys Asp Asn Lys Arg Lys Ala Phe Ser Gly
            755                 760                 765

Lys Ala Leu Ala Ile Val Gln Ser Asn Lys Leu Asp Gly Asn Ile Thr
770                 775                 780

Leu His Ala Ser Ala Glu Gly Leu Ser Ser Gly Asn Val Thr Ile Phe
785                 790                 795                 800

Thr Thr Ala Ser Ala Asp Gln Asn Ser Ile Thr Ile Ala Gly Ile Asp
                805                 810                 815

Glu Val Asn Val Leu Val Asp Phe Asn Val Val Pro Glu Leu Pro Ser
            820                 825                 830

Gln Ile Lys Val Tyr Tyr Ser Asp Ser Thr Val Glu Met Lys Pro Val
            835                 840                 845

Thr Trp Asp Ala Val Asp Pro Asn Leu Leu Asn Thr Ala Gly Lys Ile
```

```
                850             855             860
Ile Val Glu Gly Thr Val Gly Thr Asp Lys Lys Ala Lys Ala Leu
865                     870             875             880

Leu Ile Val Lys Gly Asn Gly Gln Glu Asn Ser Glu Tyr Arg Ile Asp
                885             890             895

Leu Phe Ser Pro Asp Pro Lys Leu Ile Ser Thr Glu Leu Thr Val Glu
            900             905             910

Lys Thr Asn Ile Met Glu Asp Asp Phe Ile Asp Ile Lys Val Ile Gly
        915             920             925

Gln Leu Glu Asn Lys Glu Val Val Asp Leu Ser Asn Phe Met Pro Ile
    930             935             940

Tyr Glu Phe Asp Cys Asp Ile Ile Lys Ile Glu Gly Asn Lys Leu Tyr
945             950             955             960

Ala Leu Glu Glu Gly Leu Val Lys Val Thr Ala Val Thr Tyr Lys
                965             970             975

Gly Arg Thr Val Thr Ser Pro Glu Met Met Leu Lys Ile Thr Lys Asn
                980             985             990

Pro Val Pro Lys Thr Ile Thr His  Ile Asp Ser Ile Thr Val Val Ala
            995             1000            1005

Gly Lys  Gly Glu Ala Pro Val  Leu Pro Ala Thr Ala  Val Ala His
    1010            1015            1020

Phe Asp  Arg Gly Met Pro Arg  Asp Val Lys Val Lys  Trp Glu Ile
    1025            1030            1035

Val Asn  Pro Ala Leu Tyr Gln  Asn Leu Gly Glu Phe  Thr Val Ser
    1040            1045            1050

Gly Asp  Val Glu Gly Thr Glu  Ile Lys Ala Gln Ala  Lys Val Met
    1055            1060            1065

Val Arg  Ser Ala Leu Ala Ile  Glu Thr Ile Ser Met  Ala Val Leu
    1070            1075            1080

Pro Asn  Gln Lys Pro Glu Leu  Pro Gln Lys Val Thr  Val Tyr Tyr
    1085            1090            1095

Ser Asp  Gly Thr Glu Glu Gln  Ala Asp Val Asp Trp  Asp Ala Met
    1100            1105            1110

Pro Ser  Ala Glu Leu Lys Ser  Glu Gly Val Val Lys  Val Lys Gly
    1115            1120            1125

Ser Val  Lys Gly Val Asp Leu  Lys Ala Thr Ala Gln  Ile Arg Val
    1130            1135            1140

Thr Ser  Glu Val Gly Gly Val  Gln Asn Ile Ser Arg  Ala Lys Asn
    1145            1150            1155

Gly Tyr  Glu Tyr Pro Lys Ala  Glu Ala Ser Phe Thr  Asn Thr Gly
    1160            1165            1170

Pro Gly  Ser Asn Asp Arg Ile  Glu Ala Ile Asn Asp  Asp Val Ile
    1175            1180            1185

Ser Tyr  Asp Ala Glu Pro His  Asn Arg Trp Thr Asn  Trp Gln Pro
    1190            1195            1200

Thr Pro  Arg Pro Gly Asp Trp  Val Ser Ile Thr Phe  Gly Asp Ser
    1205            1210            1215

Lys Pro  Arg Lys Tyr Asp Ile  Asp Ser Met Glu Ile  His Trp Tyr
    1220            1225            1230

Glu Asp  Leu Gly Thr Ser Ser  Pro Ala Tyr Phe Arg  Ile Gln Tyr
    1235            1240            1245

Lys Ser  Gly Asp Glu Trp Lys  Asp Val Ser Gly Leu  Lys Thr Asn
    1250            1255            1260
```

```
Pro Ser Asn Thr Val Leu Arg Gln Ala Asn Val Tyr Thr Phe Asp
    1265                1270                1275

Lys Val Arg Thr Ser Ala Ile Arg Val Asp Met Thr Ala Lys Thr
    1280                1285                1290

Gly Lys Ser Leu Ala Ile Thr Glu Ile
    1295                1300

<210> SEQ ID NO 25
<211> LENGTH: 41
<212> TYPE: DNA
<213> ORGANISM: Artificial Sequence
<220> FEATURE:
<223> OTHER INFORMATION: BgaII-1302-D92-R

<400> SEQUENCE: 25
gcgaccggcg ctcagctgtt agatctcggt gatggctaag c                    41

<210> SEQ ID NO 26
<211> LENGTH: 1350
<212> TYPE: PRT
<213> ORGANISM: Artificial Sequence
<220> FEATURE:
<223> OTHER INFORMATION: BgaII-1350

<400> SEQUENCE: 26

Met Arg Arg Ile Asn Phe Asn Asp Asn Trp Arg Phe Gln Arg Glu Ile
1               5                   10                  15

Ser Thr Ser Leu Arg Glu Ala Gln Lys Pro Ser Phe Asn Asp His Ser
            20                  25                  30

Trp Arg Gln Leu Ser Leu Pro His Asp Trp Ser Ile Glu Leu Asp Phe
        35                  40                  45

Asn Lys Asp Ser Leu Ala Thr His Glu Gly Gly Tyr Leu Asp Gly Gly
    50                  55                  60

Val Gly Trp Tyr Arg Lys Thr Phe Thr Val Pro Ser Ala Met Glu Gly
65                  70                  75                  80

Lys Arg Ile Ser Leu Asp Phe Asp Gly Val Tyr Met Asn Ser Thr Thr
                85                  90                  95

Tyr Leu Asn Gly Glu Glu Leu Gly Thr Tyr Pro Phe Gly Tyr Asn Ala
            100                 105                 110

Phe Ser Tyr Asp Ile Thr Asp Lys Leu Phe Met Asp Gly Arg Glu Asn
        115                 120                 125

Val Leu Ala Val Lys Val Asp Asn Thr Gln Pro Ser Ser Arg Trp Tyr
    130                 135                 140

Ser Gly Ser Gly Ile Tyr Arg Asn Val Tyr Leu Thr Val Thr Asn Pro
145                 150                 155                 160

Val His Val Ala Arg Tyr Gly Thr Phe Val Thr Thr Pro Asp Leu Glu
                165                 170                 175

Ser Ala Tyr Ala Ala Arg Lys Ala Glu Val Asn Ile Lys Thr Lys Ile
            180                 185                 190

Asn Asn Asp Ser Asp Ala Ala Val Gln Val Lys Val Lys Ser Thr Ile
        195                 200                 205

Tyr Asp Thr Asp Gly Lys Glu Val Ala Ser Val Ser Gln Glu Lys
    210                 215                 220

Thr Ala Ala Ala Gly Thr Thr Ala His Phe Glu Asp Asn Thr Val Ile
225                 230                 235                 240

Glu Asn Pro Glu Leu Trp Ser Leu Asp Asn Pro Tyr Arg Tyr Lys Leu
                245                 250                 255
```

```
Val Thr Asp Val Leu Ile Gly Gly Glu Thr Val Asp Thr Tyr Glu Thr
            260                 265                 270

Arg Phe Gly Ala Arg Phe Phe Lys Phe Asp Ala Asn Glu Gly Phe Ser
            275                 280                 285

Leu Asn Gly Lys Pro Met Lys Leu Tyr Gly Val Ser Met His His Asp
            290                 295                 300

Leu Gly Ala Leu Gly Ala Ala Thr Asn Ala Arg Ala Val Glu Arg Gln
305                 310                 315                 320

Leu Gln Ile Met Lys Asp Met Gly Val Asn Ala Ile Arg Gly Thr His
                325                 330                 335

Asn Pro Val Ser Pro Glu Phe Leu Glu Ala Val Asn Asn Leu Gly Leu
            340                 345                 350

Leu Leu Ile Glu Glu Ala Phe Asp Cys Trp Ser Gln Ser Lys Lys Thr
            355                 360                 365

Tyr Asp Tyr Gly Arg Phe Phe Thr Arg Trp Ala Glu His Asp Val Lys
        370                 375                 380

Glu Met Val Asp Arg Gly Lys Asn Glu Pro Ser Ile Ile Met Trp Ser
385                 390                 395                 400

Ile Gly Asn Glu Ile Tyr Asp Thr Thr Ser Pro Ser Gly Val Glu Thr
                405                 410                 415

Ala Arg Asn Leu Val Arg Trp Ile Lys Glu Ile Asp Thr Thr Arg Pro
            420                 425                 430

Thr Thr Ile Gly Glu Asp Lys Thr Arg Gly Asp Lys Val Asn Val Thr
        435                 440                 445

Pro Ile Asp Pro Asn Ile Leu Glu Ile Phe His Thr Val Asp Val Val
            450                 455                 460

Gly Leu Asn Tyr Ser Glu Asn Asn Tyr Val Gly Tyr His Glu Gln His
465                 470                 475                 480

Pro Asn Trp Lys Leu Tyr Gly Ser Glu Thr Ser Ser Ala Thr Arg Ser
                485                 490                 495

Arg Gly Val Tyr Thr His Pro Tyr Glu Tyr Asn Leu Gly Thr Lys Tyr
            500                 505                 510

Asp Asp Leu Gln Gln Ser Ser Tyr Asp Asn Asp Tyr Val Pro Trp Gly
            515                 520                 525

Arg Thr Ala Glu Asp Ala Trp Lys Ser Asp Arg Asp Leu Lys His Phe
530                 535                 540

Ala Gly Gln Phe Ile Trp Thr Gly Phe Asp Tyr Ile Gly Glu Pro Thr
545                 550                 555                 560

Pro Tyr Tyr Asp Ser Tyr Pro Ala Lys Ser Ser Tyr Phe Gly Ala Val
            565                 570                 575

Asp Thr Ala Gly Phe Pro Lys Asp Ile Phe Tyr Tyr Gln Ser Gln
            580                 585                 590

Trp Lys Lys Glu Pro Met Val His Leu Leu Pro His Trp Asn Trp Thr
            595                 600                 605

Glu Gly Glu Pro Val Arg Val Leu Ala Tyr Thr Asn Ala His Gln Val
            610                 615                 620

Glu Leu Phe Leu Asn Gly Lys Ser Leu Gly Val Arg Gly Tyr Glu Asn
625                 630                 635                 640

Lys Lys Thr Ser Trp Gly Ala Pro Tyr Lys Glu Thr Lys Asp Gly Lys
                645                 650                 655

Thr Tyr Leu Glu Trp Ala Val Pro Phe Lys Ala Gly Thr Leu Glu Ala
            660                 665                 670
```

-continued

Val Ala Met Asp Glu Asn Gly Lys Glu Ile Ala Arg Asp Gln Val Thr
            675                 680                 685

Thr Ala Gly Ala Pro Ala Val Lys Leu Thr Ala Asp Arg Lys Val
        690                 695                 700

Ile Lys Ala Asp Gly Thr Asp Leu Ser Phe Ile Thr Ala Glu Ile Val
705                 710                 715                 720

Asp Ser Lys Gly Asn Val Val Pro Asn Ala Asp His Leu Ile Gln Phe
                725                 730                 735

His Leu Ser Gly His Gly Glu Leu Gly Val Asp Asn Gly Asp Ala
            740                 745                 750

Ala Ser Val Glu Arg Tyr Lys Asp Asn Lys Lys Ala Phe Ser Gly
        755                 760                 765

Lys Ala Leu Ala Ile Val Gln Ser Asn Lys Leu Asp Gly Asn Ile Thr
        770                 775                 780

Leu His Ala Ser Ala Glu Gly Leu Ser Ser Gly Asn Val Thr Ile Phe
785                 790                 795                 800

Thr Thr Ala Ser Ala Asp Gln Asn Ser Ile Thr Ile Ala Gly Ile Asp
            805                 810                 815

Glu Val Asn Val Leu Val Asp Phe Asn Val Val Pro Glu Leu Pro Ser
        820                 825                 830

Gln Ile Lys Val Tyr Tyr Ser Asp Ser Thr Val Glu Met Lys Pro Val
        835                 840                 845

Thr Trp Asp Ala Val Asp Pro Asn Leu Leu Asn Thr Ala Gly Lys Ile
        850                 855                 860

Ile Val Glu Gly Thr Val Glu Gly Thr Asp Lys Lys Ala Lys Ala Leu
865                 870                 875                 880

Leu Ile Val Lys Gly Asn Gly Gln Glu Asn Ser Glu Tyr Arg Ile Asp
                885                 890                 895

Leu Phe Ser Pro Asp Pro Lys Leu Ile Ser Thr Glu Leu Thr Val Glu
            900                 905                 910

Lys Thr Asn Ile Met Glu Asp Asp Phe Ile Asp Ile Lys Val Ile Gly
            915                 920                 925

Gln Leu Glu Asn Lys Glu Val Val Asp Leu Ser Asn Phe Met Pro Ile
        930                 935                 940

Tyr Glu Phe Asp Cys Asp Ile Ile Lys Ile Glu Gly Asn Lys Leu Tyr
945                 950                 955                 960

Ala Leu Glu Glu Gly Leu Val Lys Val Thr Ala Ala Val Thr Tyr Lys
                965                 970                 975

Gly Arg Thr Val Thr Ser Pro Glu Met Met Leu Lys Ile Thr Lys Asn
            980                 985                 990

Pro Val Pro Lys Thr Ile Thr His Ile Asp Ser Ile Thr Val Val Ala
        995                 1000                1005

Gly Lys Gly Glu Ala Pro Val Leu Pro Ala Thr Ala Val Ala His
        1010                1015                1020

Phe Asp Arg Gly Met Pro Arg Asp Val Lys Val Lys Trp Glu Ile
        1025                1030                1035

Val Asn Pro Ala Leu Tyr Gln Asn Leu Gly Glu Phe Thr Val Ser
        1040                1045                1050

Gly Asp Val Glu Gly Thr Glu Ile Lys Ala Gln Ala Lys Val Met
        1055                1060                1065

Val Arg Ser Ala Leu Ala Ile Glu Thr Ile Ser Met Ala Val Leu
        1070                1075                1080

Pro Asn Gln Lys Pro Glu Leu Pro Gln Lys Val Thr Val Tyr Tyr

```
                    1085                1090                1095
Ser Asp Gly Thr Glu Glu Gln Ala Asp Val Asp Trp Asp Ala Met
                    1100                1105                1110
Pro Ser Ala Glu Leu Lys Ser Glu Gly Val Val Lys Val Lys Gly
                    1115                1120                1125
Ser Val Lys Gly Val Asp Leu Lys Ala Thr Ala Gln Ile Arg Val
                    1130                1135                1140
Thr Ser Glu Val Gly Gly Val Gln Asn Ile Ser Arg Ala Lys Asn
                    1145                1150                1155
Gly Tyr Glu Tyr Pro Lys Ala Glu Ala Ser Phe Thr Asn Thr Gly
                    1160                1165                1170
Pro Gly Ser Asn Asp Arg Ile Glu Ala Ile Asn Asp Asp Val Ile
                    1175                1180                1185
Ser Tyr Asp Ala Glu Pro His Asn Arg Trp Thr Asn Trp Gln Pro
                    1190                1195                1200
Thr Pro Arg Pro Gly Asp Trp Val Ser Ile Thr Phe Gly Asp Ser
                    1205                1210                1215
Lys Pro Arg Lys Tyr Asp Ile Asp Ser Met Glu Ile His Trp Tyr
                    1220                1225                1230
Glu Asp Leu Gly Thr Ser Ser Pro Ala Tyr Phe Arg Ile Gln Tyr
                    1235                1240                1245
Lys Ser Gly Asp Glu Trp Lys Asp Val Ser Gly Leu Lys Thr Asn
                    1250                1255                1260
Pro Ser Asn Thr Val Leu Arg Gln Ala Asn Val Tyr Thr Phe Asp
                    1265                1270                1275
Lys Val Arg Thr Ser Ala Ile Arg Val Asp Met Thr Ala Lys Thr
                    1280                1285                1290
Gly Lys Ser Leu Ala Ile Thr Glu Ile Lys Val Phe Ser Lys Trp
                    1295                1300                1305
Ala Lys Ala His Thr His Pro Met Val Thr Asp Ile Lys Leu Gly
                    1310                1315                1320
Asp Leu Ser Ile Leu Asp Asp Phe Ser Lys Lys Gly Asp Asn Asn
                    1325                1330                1335
Glu Leu Thr Phe Gln Val Lys Asp Pro Arg Asp Ile
                    1340                1345                1350

<210> SEQ ID NO 27
<211> LENGTH: 41
<212> TYPE: DNA
<213> ORGANISM: Artificial Sequence
<220> FEATURE:
<223> OTHER INFORMATION: BgaII-1350-D92-R

<400> SEQUENCE: 27
gcgaccggcg ctcagctgtt atatgtctct tgggtctttg a       41
```

BETA-GALACTOSIDASE VARIANT HAVING HIGH TRANSGLYCOSYLATION ACTIVITY, AND USE THEREOF

CROSS-REFERENCE TO RELATED APPLICATIONS

This application is a U.S. national phase under the provisions of 35 U.S.C. § 371 of International Patent Application No. PCT/KR2016/005335 filed May 19, 2016, which in turn claims priority of Korean Patent Application No. 10-2015-0074862 filed May 28, 2015. The disclosures of such international patent application and Korean priority patent application are hereby incorporated herein by reference in their respective entireties, for all purposes.

TECHNICAL FIELD

The present invention relates to a novel beta-galactosidase mutant, and more particularly to a beta-galactosidase mutant from *Bacillus circulans*, a gene encoding the same, a recombinant vector and a recombinant microorganism, which contain the gene, a method for producing the beta-galactosidase mutant using the recombinant microorganism, and a method for producing galacto-oligosaccharide using the beta-galactosidase mutant.

BACKGROUND ART

β-galactosidases hydrolyze non-reducing terminal β-D-galactose in β-D-galactopyranosides such as lactose to make galactose and glucose or catalyze the transition of non-reducing galactose to other compounds. Generally, such enzymes have two functions (hydrolytic activity and transglycosylation activity), but the ratio of the two reactions varies depending on the kind of β-galactosidase. The hydrolytic activity of β-galactosidases hydrolyzes lactose in milk and dairy products to prevent lactose intolerance and is used to increase the sweetness of milk or produce sweet syrup as a milk byproduct. The transglycosylation activity of β-galactosidases is used for the production of galactooligosaccharides which stimulate the growth of lactic acid bacteria that are human intestinal beneficial microorganisms. Thus, β-galactosidases are industrially very useful enzymes.

Beta-galactosidases are widely found in mammalian organs, plant seeds, bacteria, fungi, and yeasts. In the food industry, beta-galactosidases from yeasts such as *Kluyveromyces lactis* and *Kluyveromyces fragilis*, fungi such as *Aspergillus niger* and *Aspergillus oryzae*, and bacteria such as *Bacillus circulans*, have been used. Among them, beta-galactosidase from *Bacillus circulans* ATCC 31382 is commercially available under the trade name of Biolacta (Daiwa Kasei, U.S. Pat. No. 4,237,230 (1980)).

Beta-galactosidase bonds with lactose and a reaction begins while the carboxyl group of a glutamate residue in the reaction center acts as an acid/base catalyst (Juers et al., *Biochemistry*, 40, 14781-14794, 2001). This nucleophile glutamate residue attacks carbon 1 of galactose bound to glucose to detach the glucose and form a temporary covalent bond with the galactose. A hydroxyl group attached to carbon 4 of the glucose that is detached is stabilized with the aid of other glutamates functioning as an acid catalyst and then is detached from the enzyme while it is converted to free glucose by receiving a proton. The galactose forming a temporary covalent bond with the glutamate residue of the enzyme is detached from the enzyme by reaction with water (hydrolysis), or bonds to lactose or other compounds newly introduced into the reaction center of the enzyme (transgalactosylation). A substance having one or more galactose units (galactosides) produced by this transgalactosylation is known as galactooligosaccharide (GOS).

GOS acts as prebiotics that reaches the large intestines without being digested and absorbed, thereby promoting the growth and activity of intestinal useful microorganisms such as *Bifidobacteria* or *Lactobacilli*. GOS is known to have health promotion effects, including cancer prevention, mineral absorption, lipid metabolism, anti-inflammation, atopy relief and the like (Macfarlane et al., *J. Appl. Mcriobiol.*, 104, 305-344, 2008). Furthermore, it has been reported that, when a person suffering from irritable bowel syndrome takes GOS, the level of the beneficial intestinal bacteria *Bifidobacteria* is increased and symptoms of the syndrome are also alleviated (Silk et al., *Aliment. Pharmacol. Ther.*, 29, 508-518, 2009).

Currently, beta-galactosidases from *Bacillus* or *Aspergillus* are frequently used for the production of GOS. Particularly, beta-galactosidases from *Bacillus circulans* are most frequently used for commercial purposes due to their optimum activation temperature (50 to 60° C.), which is relatively high, and their high transglycosylation activity. Various beta-galactosidases, such as 240 kDa beta-galactosidase, 160 kDa beta-galactosidase (Mozafar et al., Agric. Biol. Chem., 48, 3053-3061, 1984); 212 kDa, 145 kDa, 86 kDa (Vetere and Paoletti, Biochim. Biophys. Acta, 1380, 223-231, 1998); 195 kDa, 160 kDa, 135 kDa, 86 kDa (Song et al., Biosci. Biotechnol. Biochem., 75, 268-278, 2011) and the like, derived from *Bacillus circulans*, were reported. In addition, it has been reported that new beta-galactosidase BgaII having a size of 145 kDa was found in *Bacillus circulans* (Korean Patent Registration No. 1,121,161).

Accordingly, the present inventors have made extensive efforts to develop a beta-galactosidase having an enhanced ability to produce galactooligosaccharide from lactose, and as a result, have found that, when a mutant was constructed by deleting the C-terminus of beta-galactosidase BgaII, it has an enhanced ability to produce galactooligosaccharide and has dramatically increased thermal stability, thereby completing the present invention.

DISCLOSURE OF INVENTION

Technical Problem

It is an object of the present invention to provide a beta-galactosidase mutant, a gene encoding the same, a recombinant vector containing the above-described gene, and a recombinant microorganism transformed with the recombinant vector.

Another object of the present invention is to provide a method for producing a beta-galactosidase mutant using the above-described recombinant microorganism and a method for producing a galactooligosaccharide.

Technical Solution

To achieve the above object, the present invention provides a beta-galactosidase mutant which has improved biochemical properties, including improved thermal stability or enzymatic activity, due to a C-terminal deletion mutation of a beta-galactosidase represented by an amino acid sequence of SEQ ID NO: 3.

The present invention also provides a beta-galactosidase mutant having an amino acid sequence which comprises amino acids 1 to 798 of a beta-galactosidase represented by an amino acid sequence of SEQ ID NO: 3 and which contains a C-terminal deletion mutation after any one of amino acid residues 799 to 1396.

The present invention also provides a gene encoding the above-described beta-galactosidase mutant and a recombinant vector containing the above-described gene.

The present invention also provides a recombinant microorganism wherein the above-described gene or the above-described recombinant vector is inserted into a host cell selected from the group consisting of bacteria, fungi, and yeasts.

The present invention also provides a method for producing a beta-galactosidase mutant, comprising the steps of:
culturing the recombinant microorganism of claim 7 to express a beta-galactosidase mutant; and
recovering the expressed beta-galactosidase mutant.

The present invention also provides a method for producing a galactooligosaccharide, comprising:
reacting the above-described beta-galactosidase mutant with a lactose-containing substrate to produce galactooligosaccharide; and
recovering the produced galactooligosaccharide.

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods, which will be described below, are those well-known and commonly employed in the art.

In the present invention, it was found that, when mutants were constructed by deleting the C-terminus of the beta-galactosidase discovered in a previous patent (Korean Patent Registration No. 1,121,161), they had increased transglycosylation activity and thermal activity.

Figure 1:
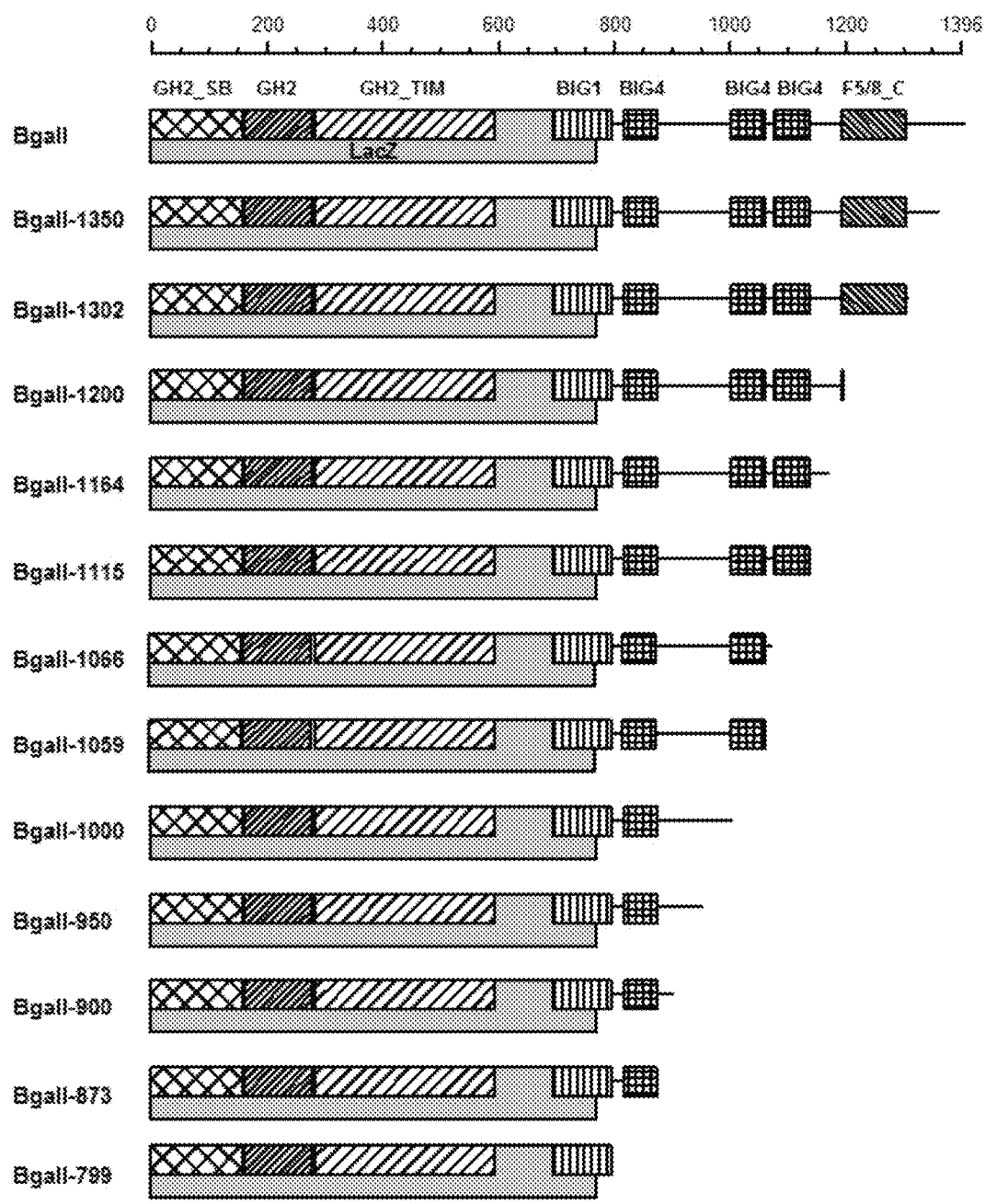
FIG. 1 shows conserved domains of the amino acid sequences of beta-galactosidase and its mutants.

In the present invention, it could be seen that the domains of the beta-galactosidase discovered in the previous patent (Korean Patent Registration No. 1,121,161) have multiple domain structures as shown in FIG. 1. The LacZ domain of the beta-galactosidase, which consists of GH2_SB, GH2 and GH2_TIM, is a portion having enzymatic activity. The beta-galactosidase has one BIG1 and three BIG4, bacteria Ig-like domains in the C-terminus, and also has an F5/8_C domain, called "discoidin" domain, in the proximal C-terminus. Polypeptide chains having no particular structure connect between the domains, and are about 10, 50 and 130 amino acid residues in length. Furthermore, it was found that a polypeptide chain which is about 100 amino acid residues in length is present after the F5/8_C domain in the C-terminus. The domains in the C-terminus were sequentially deleted to thereby construct mutants, and the activities and thermal stabilities of the mutants were measured. As a result, it was shown that the beta-galactosidase mutants cleaved in the C-terminus had increased enzymatic activity and thermal stability. Specifically, in one example of the present invention, C-terminal deletion mutants of beta-galactosidase were constructed, and the enzymatic activities and thermal stabilities of the constructed mutants were analyzed, and as a result, it could be seen that the constructed mutants have very excellent effects.

Therefore, in one aspect, the present invention is directed to a beta-galactosidase mutant which has improved biochemical properties, including improved thermal stability or enzymatic activity, due to a C-terminal deletion mutation of a beta-galactosidase represented by an amino acid sequence of SEQ ID NO: 3.

In the present invention, the C-terminal deletion mutation may include a C-terminal deletion mutation after any amino acid residue in a range that does not impair the enzymatic activity of the beta-galactosidase represented by the amino acid sequence of SEQ ID NO: 3.

In another aspect, the present invention is directed to a beta-galactosidase mutant having an amino acid sequence which comprises amino acids 1 to 798 of a beta-galactosidase represented by an amino acid sequence of SEQ ID NO: 3 and which contains a C-terminal deletion mutation after any one of amino acid residues 799 to 1396.

In the present invention, the mutation may comprise one or more selected from the group consisting of: a) a C-terminal deletion mutation after amino acid residue 799; b) a C-terminal deletion mutation after amino acid residue 873; c) a C-terminal deletion mutation after amino acid residue 900; d) a C-terminal deletion mutation after amino acid residue 950; e) a C-terminal deletion mutation after amino acid residue 1000; f) a C-terminal deletion mutation after amino acid residue 1059; g) a C-terminal deletion mutation after amino acid residue 1066; h) a C-terminal deletion mutation after amino acid residue 1115; i) a C-terminal deletion mutation after amino acid residue 1164; j) a C-terminal deletion mutation after amino acid residue 1200; k) a C-terminal deletion mutation after amino acid residue 1302; and l) a C-terminal deletion mutation after amino acid residue 1350, but is not limited thereto.

In the present invention, the amino acid sequence of the mutant may be SEQ ID NOs: 4, 6, 8, 10, 12, 14, 16, 18, 20, 22, 24 or 26.

In still another aspect, the present invention is directed to a gene encoding the above-described beta-galactosidase mutant.

In yet another aspect, the present invention is directed to a recombinant vector comprising the above-described gene encoding the beta-galactosidase mutant, and a recombinant microorganism wherein the above-described gene or the above-described recombinant vector is inserted into a host cell selected from the group consisting of bacteria, fungi, and yeasts.

As used herein, the term "vector" means a DNA construct containing a DNA sequence operably linked to a suitable control sequence capable of effecting the expression of the DNA in a suitable host. The vector may be a plasmid, a phage particle, or simply a potential genomic insert. Once incorporated into a suitable host, the vector may replicate and function independently of the host genome, or may in some instances, integrate into the genome itself. In the present specification, "plasmid" and "vector" are sometimes used interchangeably, as the plasmid is the most commonly used form of vector. However, the present invention is intended to include other types of vectors with the same function as that would be known or known in the art. Protein expression vectors that are used in *E. coli* include pET series (Novagen, USA), pBAD series (Invitrogen, USA), pHCE or pCOLD (Takara, Japan), pACE series (Genofocus, Korea), and the like. In *Bacillus subtillis*, a target gene can be inserted into a specific portion of the genome to achieve protein expression, or pHT series vectors (MoBiTech, Germany) or the like can be used. The protein expression can be achieved using a genome-inserted or self-replicating vector in fungi or yeasts. A plant protein expression vector can be used using a T-DNA system such as *Agrobacterium tumefaciens* or *Agrobacterium rhizogenes*. Typical expression vectors for mammalian cell culture expression are based on, for example, pRK5 (EP 307,247), pSV16B (WO91/08291), and pVL1392 (Pharmingen).

As used herein, the term "expression control sequence" refers to the DNA sequences essential for the expression of the coding sequence operably linked in a particular host organism. Such control sequences include a promoter for performing transcription, any operator sequence for controlling such transcription, a sequence for encoding a suitable mRNA ribosomal binding site, and a sequence for controlling the termination of transcription and translation. For example, control sequences suitable for prokaryotes include a promoter, an arbitrary operator sequence, and a ribosomal binding site. Eukaryotic cells include promoters, polyadenylation signals, and enhancers. The factor having the greatest effect on the expression level of the gene in the plasmid is a promoter. SRα promoter, cytomegalovirus promoter and the like are preferably used as a promoter for high expression.

To express the DNA sequence of the present invention, any of a wide variety of expression control sequences may be used in the vector. Examples of useful expression control sequences include, for example, the early and late promoters of SV40 or adenovirus, the lac system, the trp system, the TAC or TRC system, the major operator and promoter regions of phage lambda, the control regions of fd coat protein, the promoter for 3-phosphoglycerate kinase or other glycolytic enzymes, the promoters of acid phosphatase, e.g., Pho5, the promoters of the yeast α-mating system, and other sequences known to control the expression of genes of prokaryotic or eukaryotic cells or their viruses, and various combinations thereof. T7 RNA polymerase promoter 010 may be effectively used to express the protein NSP in *E. coli*.

A nucleic acid is operably linked when it is placed in a functional relationship with another nucleic acid sequence. The nucleotide sequence may be a gene and a control sequence(s) linked to being capable of expressing the gene when it binds to a control sequence(s) (e.g., transcription-activating protein). For example, DNA for a pre-sequence or a secretory leader is operably linked to DNA encoding polypeptide when expressed as pre-protein participating in secretion of polypeptide; a promoter or an enhancer is operably linked to a coding sequence when affecting the transcription of the sequence; and a RBS is operably linked to a coding sequence when affecting the transcription of the sequence, or to a coding sequence when arranged to facilitate translation. Generally, the term "operably linked" means that the DNA linked sequences are contiguous, and in the case of the secretory leader, are contiguous and present in a reading frame. However, an enhancer is not necessarily contiguous. The linkage between these sequences is performed by ligation at a convenient restriction enzyme site. However, when the site does not exist, a synthetic oligonucleotide adaptor or a linker is used according to a conventional method.

The term "expression vector" as used herein generally means a double-stranded DNA fragment functioning as a recombinant carrier into which a heterologous DNA fragment is inserted. Here, the heterologous DNA means a hetero-type DNA, which is not naturally found in a host cell. The expression vector may be self-replicable regardless of host chromosomal DNA once in a host cell and may produce several copies of the vector and (heterologous) DNA inserted thereinto.

As is well known in the art, in order to increase the expression level of a transfected gene in a host cell, a corresponding gene should be operably linked to transcription and translation expression control sequences which are operated in a selected expression host. Preferably, the expression control sequences and the corresponding gene are included in one expression vector together with a bacterial selection marker and a replication origin. When an expression host cell is a eukaryotic cell, an expression vector should further include an expression marker which is useful in a eukaryotic expression host.

The host cell transformed or transfected by the aforementioned expression vector constitutes another aspect of the present invention. As used herein, the term "transformation" means that DNA can be replicated as a factor outside of chromosome or by means of completion of the entire chromosome by introducing DNA as a host. As used herein, the term "transfection" means that an expression vector is accepted by a host cell regardless of whether or not any coding sequence is actually expressed.

Of course, it should be understood that all vectors and expression control sequences do not equally function to express DNA sequences according to the present invention. Similarly, all hosts do not equally function with respect to the same expression system. However, one skilled in the art may appropriately select from among various vectors, expression control sequences, and hosts without either departing from the scope of the present invention or bearing excessive experimental burden. For example, a vector must be selected considering a host cell, because the vector must be replicated in the host cell. Specifically, the copy number of the vector, the ability of regulating the copy number and the expression of other protein encoded by the corresponding vector (e.g., the expression of an antibiotic marker) should also be considered. Also, an expression control sequence may be selected taking several factors into consideration. For example, relative strength, control capacity and compatibility with the DNA sequence of the present invention of the sequence should be deliberated particularly with respect to possible secondary structures. Further, the selection of a host cell may be made under consideration of compatibility with a selected vector, toxicity of a product encoded by a DNA sequence, secretory nature of the product, ability to correctly fold a polypeptide, fermentation or cultivation requirements, ability to ensure easy purification of a product encoded by a DNA sequence, or the like. Within the scope of these parameters, one of ordinary skill in the art may select various vectors/expression control sequences/host combinations that can express the DNA sequences of the invention in either large scale animal culture or fermentation. In cloning the cDNA of an NSP protein by the expression cloning strategy, screening procedures such as a binding method, a panning method, and a film emulsion method can be used.

In the definition of the present invention, the term "substantially pure" means that a polypeptide according to the present invention and the DNA sequences encoding the polypeptide substantially does not contain any other proteins derived from bacteria.

As host cells for expressing recombinant proteins, prokaryotic cells, such as E. coli and Bacillus subtilis, which can be cultured at a high concentration within a short time, easily genetically modified and have well established genetic and physiological properties, have been widely used. However, to solve various problems, including the post-translational modification, secretion, three-dimensional active structure and activation of proteins, a wide range from microorganisms to higher organisms, including unicellular eukaryotic cells, yeasts (Pichia pastoris, Saccharomyces cerevisiae, Hansenula polymorpha, etc.), filamentous fungi, insect cells, plant cells, and mammalian cells, has recently been used as host cells for recombinant protein production. Thus, it will be obvious to one skilled in the art to use not only E. coli cells illustrated in Examples, but also other host cells.

In a further aspect, the present invention is directed to a method for producing a beta-galactosidase mutant using the transformed recombinant microorganism, and specifically to a method for producing a beta-galactosidase mutant, comprising the steps of: culturing the recombinant microorganism to express a beta-galactosidase mutant; and recovering the expressed beta-galactosidase mutant.

The culture of the transformed recombinant microorganism is performed according to a method that is well-known in the art, and culture temperature and time, pH of a medium and the like can be adjusted properly.

Recovery of the beta-galactosidase mutant from the cultured recombinant microorganism may be performed using conventional biochemical isolation techniques, for example, treatment with a protein precipitating agent (salting out), centrifugation, ultrasonic disruption, ultrafiltration, dialysis, molecular sieve chromatography (gel filtration), adsorption chromatography, ion exchange chromatography, affinity chromatography and the like. Typically, a combination of these techniques is used to separate a protein with high purity.

Figure 2:
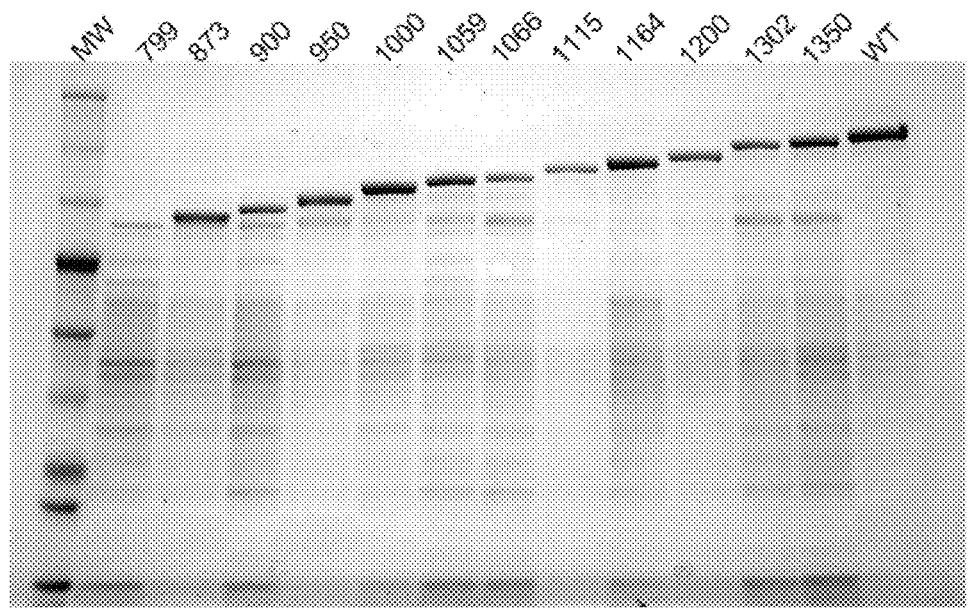
FIG. 2 shows the results obtained by performing SDS-PAGE of beta-galactosidase and its mutants, followed by staining with Coomassie brilliant blue (MW: protein size marker; WT: wild type; 799 to 1350: mutants).
Figure 3:
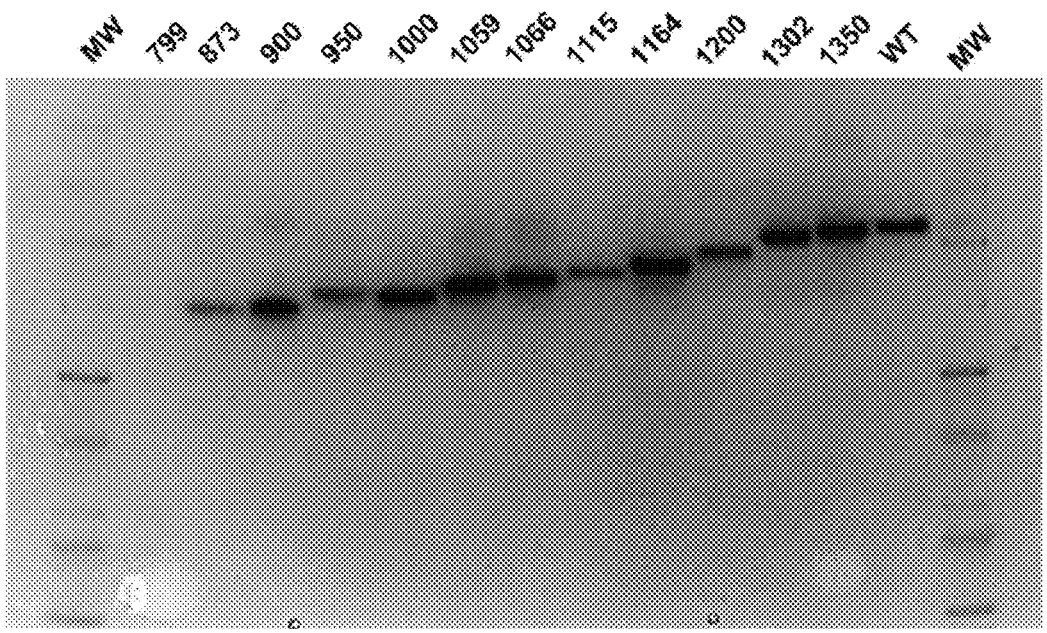
FIG. 3 shows the results obtained by performing SDS-PAGE of beta-galactosidase and its mutants, followed by staining with X-gal (MW: marker; WT: wild type; 799 to 1350: mutants).

In one example of the present invention, recombinant beta-galactosidase wild-type and mutants were constructed using transformed recombinant Bacillus subtilis, and the pD92 vector (Korean Patent Application Publication No. 10-2011-0102862) makes it possible to produce a recombinant protein in a state in which cell growth and protein expression are separated from each other, by microbial culture alone without needing to add a separator inducer for protein expression. The results of SDS-PAGE analysis of the recombinant beta-galactosidase wild-type and mutants produced by the above-described method indicated that they had expected sizes, and the results of X-gal staining of the recombinant beta-galactosidase wild-type and mutants indicated that the wild-type and mutants showed beta-galactosidase activity (FIGS. 2 and 3).

Figure 4:
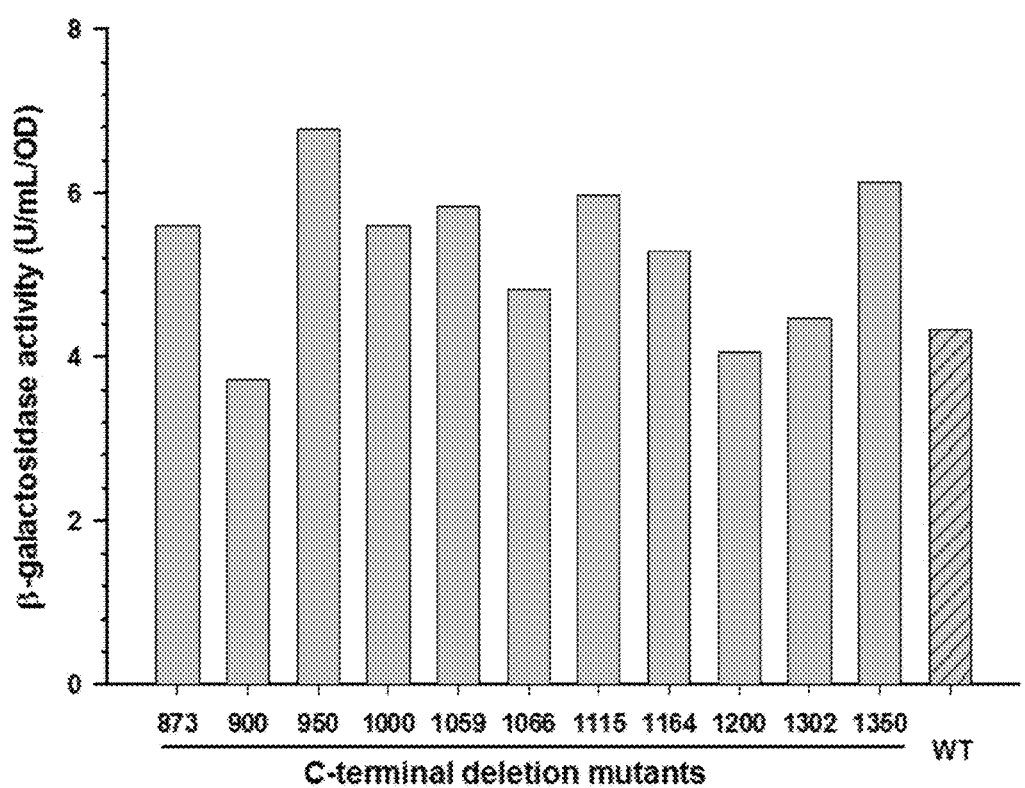
FIG. 4 shows the results of measuring the enzymatic activities of beta-galactosidase and its mutants (WT: wild type; 873 to 1350: mutants).
Figure 5:
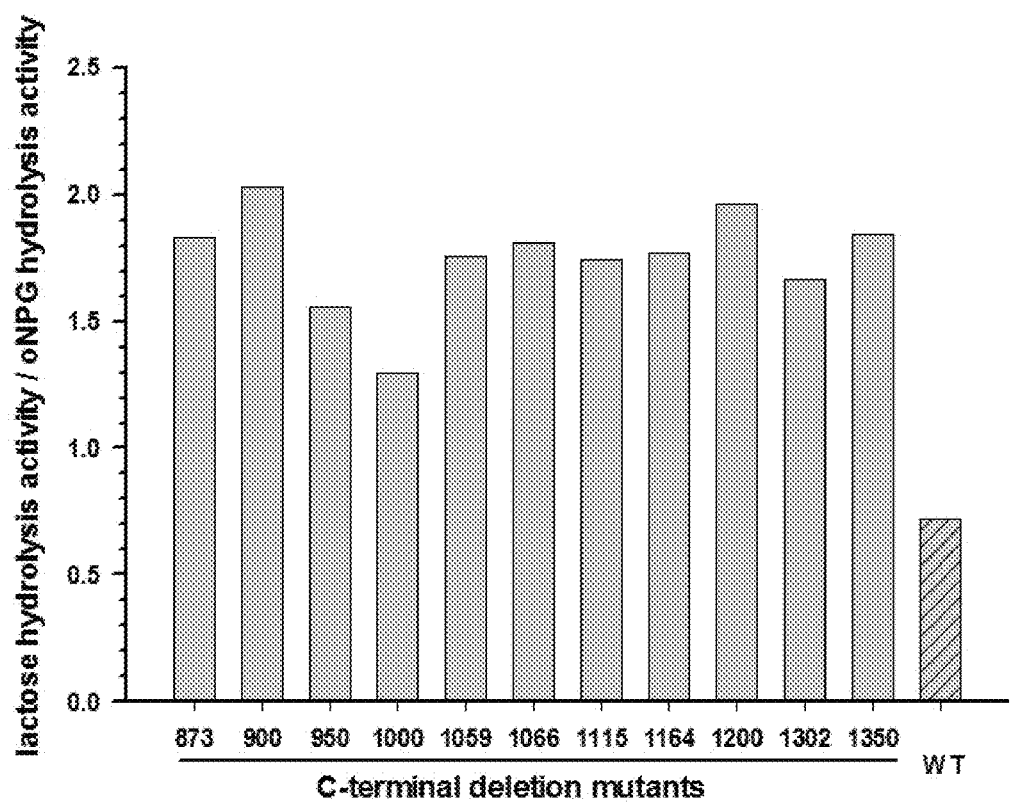
FIG. 5 shows the results of measuring the substrate specificities of beta-galactosidase and its mutants by use of oNPG and lactose (WT: wild type; 873 to 1350: mutants).
Figure 6:
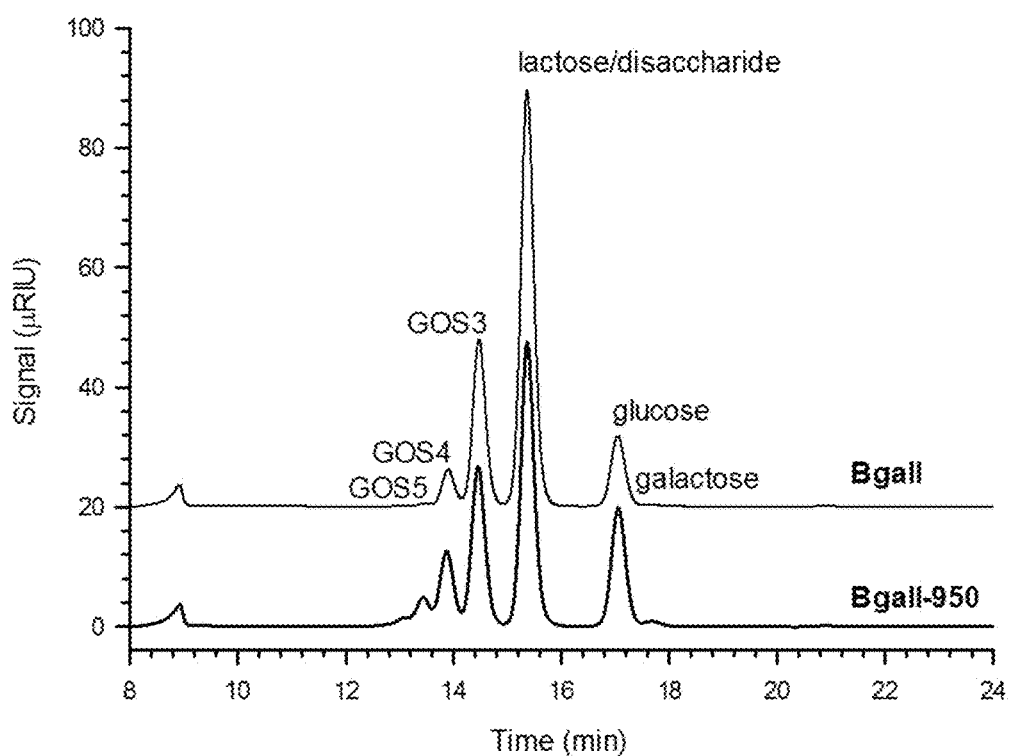
FIG. 6 shows the results of HPLC analysis of carbohydrates produced by beta-galactosidase and its mutant (BgaII: wild type; BgaII-950: mutant).

In another example of the present invention, the enzymatic activities of the obtained recombinant beta-galactosidase wild-type and mutants were measured using o-Nitrophenyl-Galactopyranoside (oNPG) as a substrate, and as a result, it was shown that the activities of the beta-galactosidase mutants were better than that of the wild type (FIG. 4). Furthermore, the substrate specificities of the recombinant beta-galactosidase wild-type and mutants were analyzed using lactose and oNPG, and as a result, it was shown that the substrate specificities of the mutants for lactose were better than that of the wild type (FIG. 5). In addition, carbohydrates produced by the recombinant beta-galactosidase wild-type and mutants were analyzed by HPLC, and as a result, it was shown that galactooligosaccharide was produced by all the wild type and the mutants, and the amount of galactooligosaccharide produced was significantly larger in the mutants than in the wild type (FIG. 6).

Figure 7:
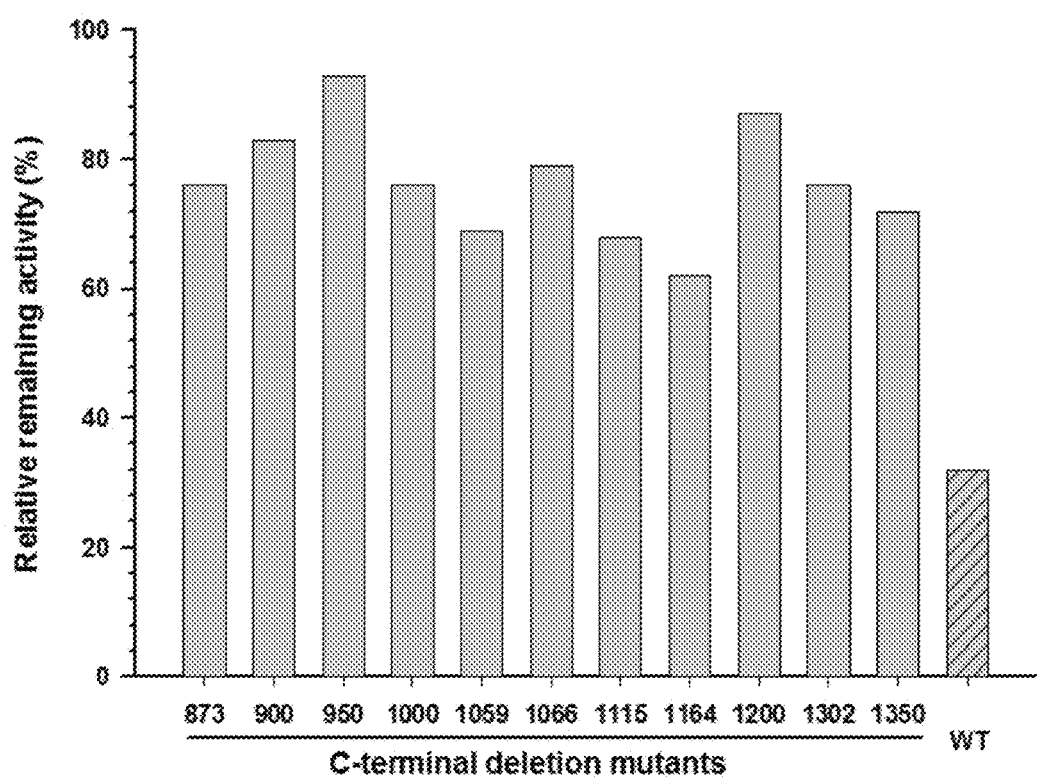
FIG. 7 shows the results of measuring the thermal stabilities of beta-galactosidase and its mutants (WT: wild type; 873 to 1350: mutants).

In another embodiment of the present invention, the recombinant beta-galactosidase wild-type and mutants were heat-treated for 1 hour at 60° C. which is higher than the optimum activation temperature (50° C.), and then the residual enzymatic activities thereof were measured using oNPG as a substrate. As a result, the residual enzymatic activities of the mutants were better than that of the wild type (FIG. 7).

In a still further aspect, the present invention is directed to a method for producing a galactooligosaccharide, comprising: reacting the above-described beta-galactosidase mutant with a lactose-containing substrate to produce galactooligosaccharide; and recovering the produced galactooligosaccharide.

In the present invention, the lactose-containing substrate means a lactose solution having a concentration of 30-60% (w/v), preferably 45-55%, most preferably 50%. As the content of lactose increases, its solubility decreases. Thus, the preparation of the lactose solution having a concentration of 540% is performed under high temperature. The galactooligosaccharide synthesis temperature preferably is 50° C. or higher, preferably 60-70° C. when a lactose solution of a high concentration is used.

In the present invention, the galactooligosaccharide may be any one ingredient selected from the group consisting of liquid milk, dried milk powder, baby milk, baby formula, ice cream, yoghurt, cheese, fermented dairy products, beverages, infant foods, cereals, bread, biscuits, confectionary, cakes, food supplements, dietary supplements, probiotic comestible foods, prebiotic comestible foods, animal feeds, poultry feeds, and drugs.

As used herein, the term "probiotics" means dietary supplements containing potentially beneficial bacteria or yeast with lactic acid bacteria as the most common microbes used. Probiotics can convert lactic acid to other carbohydrates and sugars, and thus have been used in the food industry over a long time. Probiotics give a sour taste to fermented dairy products such as yogurt, repair damaged tissue for growth, and lower pH to prevent spoilage. The most common forms of probiotics are fermented dairy products and probiotics-enriched foods, and lactic acid bacteria in Kefir (fermented milk beverage), yogurt, Sauerkraut (fermented German cabbage dish), Korean kimchi and the like were shown to have health effects similar to those of probiotics.

As used herein, the term "prebiotics" refers to substances that beneficially affect the human body by selectively stimulating the growth of a limited number of bacteria in the colon, and are composed of oligosaccharides that are not digested in the human body. Prebiotics have anti-carcinogenic, antimicrobial, hypolipidemic and glucose modulatory activities. Prebiotics may be defined as non-digestible food ingredients that beneficially affect the human body by selectively stimulating the growth of a limited number of bacteria in the colon. Prebiotics are mainly composed of oligosaccharides, including fructo-oligosaccharides, inulin, isomalto-oligosaccharides, lactilol, lactosucrose, lactulose, pyrodextrins, soy oligosaccharides, and xylo-oligosaccharides. These oligosaccharides are mainly used as bifidogenic factors to stimulate the growth of Bifidobacteria.

EXAMPLES

Hereinafter, the present invention will be described in further detail with reference to examples. It will be obvious to a person having ordinary skill in the art that these examples are for illustrative purposes only and are not to be construed to limit the scope of the present invention.

Experimental Method

E. coli Strain and Growth Conditions

Using E. coli DH5a (Enzynomics, Korea), a plasmid was constructed or separated. Bacteria were grown in LB medium, and if necessary, suitable amounts of antibiotics, including 100 μg/mL ampicillin, 5 μ/mL chloramphenicol and the like, were used.

Using Bacillus subtilis DB104 transformed with the constructed plasmid, the protein was expressed. Bacillus subtilis DB104 was cultured in LB medium for 12 hours and centrifuged at 3500 rpm for 10 minutes to precipitate cells. The cell pellets were lysed in cell lysis buffer (100 mM sodium phosphate pH 7.0, Triton X-100 1%, 1 mg/mL lysozyme, 1 U/mL DNaseI) and incubated at room temperature for 30 minutes. The cell lysate was centrifuged at 13,000 rpm for 5 minutes to remove cell debris.

DNA-Related Experimental Conditions

Restriction enzymes for DNA cleavage were purchased from Enzynomics (Korea) and used according to the manufacturer's instructions. Using a plasmid mini-prep kit (ELPIS Biotech, Korea) and a DNA gel purification kit, a plasmid was purified from E. coli and electrophoresed, and then DNA bands were purified. The DNA nucleotide sequence was analyzed by Genotech (Korea), and oligonucleotides were synthesized. To determine DNA concentrations, NanoDrop (Thermo Scientific, USA) was used. To amplify DNA, PCR-2000 (Bioneer, Korea) instrument and pfu DNA polymerase (Sungenetics, Korea) were used.

Example 1: Construction of Wild-Type Beta-Galactosidase (BgaII) Protein Expression Vector and Producing Strain In order to express wild-type beta-galactosidase BgaII in Bacillus subtilis DB104, a plasmid for insertion into the chromosome of Bacillus subtilis was constructed. Using pACE-BgaII (Korean Patent Registration No. 1,121,161) as a template, polymerase chain reaction (PCR) was used using oligonucleotides of SEQ ID NO: 1 and SEQ ID NO: 2 as primers. For PCR, 1 ng of pACE-BgaII 1 ng, 5 μL of 10-fold pfu DNA polymerase reaction buffer, 5 units of pfu DNA polymerase, 2 mM dNTP, 50 pmol of an oligonucleotide of SEQ ID NO: 1, and 50 pmol of an oligonucleotide of SEQ ID NO: 2 were mixed with one another to make a total volume of 50 μL. The PCR for DNA amplification was performed under the following conditions: DNA denaturation at 94° C. for 1 min; and 35 cycles, each consisting of 94° C. for 30 sec, 57° C. for 30 sec and 72° C. for 4 min; and the final extension at 72° C. for 7 min. The amplified DNA was electrophoresed on 1% agarose gel to purify an amplified DNA band at about 4 kb. As a vector for insertion into the chromosome of Bacillus subtilis, pD92 (Korean Patent Laid-Open Publication No. 10-2011-0102862) having a cry3Aa promoter variant was used. pD92 isolated from E. coli was double-cleaved with the restriction enzymes BamHI and PvuII and purified. 100 ng of the cleaved plasmid and 100 ng of the amplified DNA fragment were ligated with each other by use of 2.5 U of T4 DNA polymerase (ELPIS Biotech) and transformed into E. coli DH5a by heat shock. A transformed E. coli colony growing on solid LB medium containing antibiotic ampicillin was selected and grown in 5 mL of liquid LB medium, and then the plasmids were purified using a plasmid mini-prep kit. The plasmids were cleaved with the restriction enzyme Hind III, and a correct plasmid was selected and transformed into Bacillus subtilis DB104 by natural transformation. A Bacillus subtilis colony growing on solid LB medium containing 5 μg/mL of antibiotic chloramphenicol 5 μg/mL was grown again on solid LB medium containing 1% starch. The starch was stained with a solution containing 1% KI and 1% $I_2$, and a Bacillus subtilis colony not stained with the solution was selected and used as a strain for producing a wild-type beta-galactosidase of SEQ ID NO: 3.

SEQ ID NO: 1
A GGAAGAAAAG GATCC ATGAGACGAA TTAATTTTAA TG

SEQ ID NO: 2
GCGACCGGCG CTCAGCTGTC ATTCTGTAAA ACGAATG

Example 2: Construction of Vectors Expressing C-Terminal Deletion Mutant Beta-Galactosidase (BgaII) Proteins, and Producing Strains In order to construct vectors expressing C-terminal deletion mutant beta-galactosidase proteins, vectors and producing strains were constructed using pACE-BgaII (Korean Patent Registration No. 1,121,161) as a template and primer pairs shown in Table 1 below (FIG. 1).

TABLE 1

Amino Acid SEQ ID NOs of Mutants and Primers

| Mutant name | Mutant's SEQ ID NO: | Forward primer | Backward primer |
|---|---|---|---|
| BgaII-799 | SEQ ID NO: 4 | SEQ ID NO: 1 | SEQ ID NO: 5 |
| BgaII-873 | SEQ ID NO: 6 | SEQ ID NO: 1 | SEQ ID NO: 7 |
| BgaII-900 | SEQ ID NO: 8 | SEQ ID NO: 1 | SEQ ID NO: 9 |
| BgaII-950 | SEQ ID NO: 10 | SEQ ID NO: 1 | SEQ ID NO: 11 |
| BgaII-1000 | SEQ ID NO: 12 | SEQ ID NO: 1 | SEQ ID NO: 13 |
| BgaII-1059 | SEQ ID NO: 14 | SEQ ID NO: 1 | SEQ ID NO: 15 |
| BgaII-1066 | SEQ ID NO: 16 | SEQ ID NO: 1 | SEQ ID NO: 17 |
| BgaII-1115 | SEQ ID NO: 18 | SEQ ID NO: 1 | SEQ ID NO: 19 |
| BgaII-1164 | SEQ ID NO: 20 | SEQ ID NO: 1 | SEQ ID NO: 21 |
| BgaII-1200 | SEQ ID NO: 22 | SEQ ID NO: 1 | SEQ ID NO: 23 |
| BgaII-1302 | SEQ ID NO: 24 | SEQ ID NO: 1 | SEQ ID NO: 25 |
| BgaII-1350 | SEQ ID NO: 26 | SEQ ID NO: 1 | SEQ ID NO: 27 |

For PCR, 1 ng of pACE-BgaII, 5 μL of 10-fold pfu DNA polymerase chain buffer, 5 units of pfu DNA polymerase, 2 mM dNTP, 50 pmol of an oligonucleotide of SEQ ID NO: 1 and 50 pmol of a forward/reverse primer oligonucleotide were mixed with one another to make a total volume of 50 μL. PCR for DNA amplification was performed under the following conditions: DNA denaturation at 94° C. for 1 min; 35 cycles, each consisting of 94° C. for 30 sec, 57° C. for 30 and 72° C. for 4 min; and the final extension at 72° C. for 7 min. The amplified DNA was electrophoresed on 1% agarose gel to purify an amplified DNA band.

As a vector for insertion into the chromosome of *Bacillus subtilis*, pD92 having a cry3Aa promoter variant was used. pD92 (Korean Patent Laid-Open Publication No. 10-2011-0102862) isolated from *E. coli* was double-cleaved with the restriction enzymes BamHI and PvuII and purified. 100 ng of the cleaved plasmid and 100 ng of the amplified DNA fragment were ligated with each other by use of 2.5 U of T4 DNA polymerase (ELPIS Biotech) and transformed into *E. coli* DH5a by heat shock. A transformed *E. coli* colony growing on solid LB medium containing antibiotic ampicillin was selected and grown in 5 mL of liquid LB medium, and then the plasmids were purified using a plasmid miniprep kit. The plasmids were cleaved with the restriction enzyme Hind III, and a correct plasmid was selected and transformed into *Bacillus subtilis* DB104 by natural transformation. A *Bacillus subtilis* colony growing on solid LB medium containing 5 μg/mL of antibiotic chloramphenicol 5 μg/mL was grown again on solid LB medium containing 1% starch. The starch was stained with a solution containing 1% KI and 1% $I_2$, and a *Bacillus subtilis* colony not stained with the solution was selected and used as a strain for producing a wild-type beta-galactosidase of SEQ ID NO: 3.

Example 3: Expression and Confirmation of Wild-Type and C-Terminal Deletion Mutant Beta-Galactosidase (BgaII) Proteins

*Bacillus subtilis* DB104 cells producing each of wild-type and C-terminal deletion mutant beta-galactosidase proteins were plated on solid LB medium containing 5 μg/mL of chloramphenicol and were grown as single colonies in an incubator at 37° C. Every single colony was inoculated into 5 mL of liquid medium and cultured in a shaking incubator at 37° C. 0.5 mL of the seed culture was inoculated into 50 mL of liquid LB medium containing 5 μg/mL of chloramphenicol and was cultured in a shaking incubator at 37° C. The culture was centrifuged at 3,500 rpm for 10 minutes to separate the cells from the medium. The cell pellets were lysed in cell lysis buffer (100 mM sodium phosphate pH 7.0, Triton X-100 1%, lysozyme 1 mg/mL, DNaseI 1 U/mL) and incubated at room temperature for 30 minutes. The cell lysate was centrifuged at 13,000 rpm for 5 minutes to remove cell debris. In order to analyze the composition of proteins in the cell lysate, 5-fold gel loading buffer and the sample were mixed at a ratio of 1:4, boiled for 5 minutes and then subjected to SDS-PAGE on 4-20% acrylamide gel (Bio-Rad, USA). The gel was stained with colloidal blue. Using a stained protein molecular weight marker (ElpisBiotech, Korea), the relative sizes of the wild-type and C-terminal deletion mutant beta-galactosidase (BgaII) proteins were measured.

As shown in FIG. 2, wild-type beta-galactosidase II could be confirmed by a thick protein band at about 150 kD. The C-terminal deletion mutant beta-galactosidase (BgaII) proteins, BgaII-873, BgaII-900, BgaII-950, BgaII-1000, BgaII-1059, BgaII-1066, BgaII-1115, BgaII-1064, BgaII-1200, BgaII-1302 and BgaII-1350 could also be confirmed by stepped thick protein bands on the stained gel. It was shown that BgaII-799 was weakly expressed.

In order to confirm that the thick protein bands on the gel stained with colloidal blue are wild-type and C-terminal deletion mutant beta-galactosidase (BgaII) proteins, the protein gel after SDS-PAGE was incubated in x-gal solution (Sigma Alrich, USA) which is a beta-galactosidase developing reagent. The cell lysate and a gel loading buffer containing 0.5% sodium dodecyl sulfate were mixed with each other at a ratio of 4:1, and then subjected to SDS-PAGE on 4-20% acrylamide gel (Bio-Rad, USA). The electrophoresis was performed at 50 V to minimize protein denaturation caused by heat generation. After completion of the electrophoresis, the gel was washed three times with saline, and then a beta-galactosidase reaction was performed in a saline containing 1 mg/mL x-gal to make a blue band (that is an enzymatic reaction product on the protein electrophoresis gel.

As shown in FIG. 3, the C-terminal deletion mutant beta-galactosidase (BgaII) proteins, BgaII-873, BgaII-900, BgaII-950, BgaII-1000, BgaII-1059, BgaII-1066, BgaII-1115, BgaII-1064, BgaII-1200, BgaII-1302, BgaII-1350, and the wild-type beta-galactosidase could be confirmed by upwardly stepped blue bands. In the cell lysate sample containing BgaII-799, a faint blue band could be observed.

Example 4: Measurement of Activities of Wild-Type and C-Terminal Deletion Mutant Beta-Galactosidase (BgaII) Proteins—oNPG Method At 10 minutes before an activity measurement experiment, a test tube containing 1.5 mL of 100 mM phosphate acetate containing 1 mM o-nitrophenol galactopyranoside (oNPG) was pre-warmed in a water bath at 50° C. Then, 50 μL of a sample was added to the test tube and allowed to react for 10 minutes. Next, 10% sodium carbonate was added to terminate the reaction, and the test tube was cooled to room temperature. The absorbance at 420 nm was measured. Varying concentrations of o-nitrophenol solution were made to prepare a concentration standard curve. Using the slope of the graph, the concentration of the beta-galactosidase reaction product was determined. 1 U of beta-galactosidase was defined as an activity that makes 1 mol of o-nitrophenol for 1 minute.

In order to examine the production of the wild-type and C-terminal deletion mutant beta-galactosidase proteins, the cellular amount and enzymatic activity of the beta-galactosidase producing strain were measured in LB medium. *Bacillus subtilis* DB104 cells were plated on solid LB medium containing 5 μg/mL of antibiotic chloramphenicol and were grown as single colonies in an incubator at 37° C. Every single colony was inoculated into 5 mL of liquid medium and cultured in a shaking incubator at 37° C. 0.5 mL of the seed culture was inoculated into 50 mL of liquid LB medium containing 5 μg/mL of antibiotic chloramphenicol and was cultured in a shaking incubator at 37° C. The culture was taken and diluted 10-fold, and then the absorbance at a wavelength of 600 nm was measured to the amount of the cells. The culture was centrifuged at 3,500 rpm for 10 minutes to separate the cells from the medium. The cell pellets were lysed in cell lysis buffer (100 mM sodium phosphate pH 7.0, Triton X-100 1%, 1 mg/mL lysozyme, 1 U/mL DNaseI) and incubated at room temperature for 30 minutes. The cell lysate was centrifuged at 13,000 rpm for 5 minutes to remove cell debris. The activity of beta-galactosidase in the supernatant was measured by the oNPG method to determine the specific activity (U/mL), and then the specific activity was divided by the absorbance corresponding to the amount of the cells, thereby determining beta-galactosidase activity (U/mL/OD).

As shown in FIG. 4, BgaII-1066, BgaII-1200, BgaII-1302 and wild-type beta-galactosidase showed similar enzymatic activities (about 4 U/mL/OD). BgaII-900 showed an enzymatic activity which was about 10% lower than the wild-type beta-galactosidase. BgaII-870, BgaII-950, BgaII-950, BgaII-1000, BgaII-1059, BgaII-1115, BgaII-1064, and BgaII-1305 showed beta-galactosidase activities which were about 20% higher than the wild-type beta-galactosidase.

Example 5: Measurement of Substrate Specificities of Wild-Type and C-Terminal Deletion Mutant Beta-Galactosidase (BgaII) Proteins First, the concentration of glucose produced by the hydrolysis of lactose by beta-galactosidase was measured to determine the lactose hydrolysis activity of the beta-galactosidase. 1 U was defined as an activity that makes 1 mol of glucose for 1 minute.

Using 100 mM phosphate acetate buffer, 5% lactose solution was made. A test tube containing 1.5 mL of the lactose solution was pre-warmed in a water bath at 50° C. Then, 50 µL of a sample was added to the test tube and allowed to react for 10 minutes. The test tube was immersed in boiling water for 5 minutes to stop the enzymatic reaction. To measure the concentration of glucose in the solution, 50 µL of a glucose measurement reaction solution was mixed with 50 µL of a glucose measurement solution and incubated in an incubator at 37° C. for 1 hour. The glucose measurement reaction solution was prepared by mixing glucose oxidase, dianisidine and hydrogen peroxidase in 100 mM potassium phosphate buffer (pH 6.0). 100 µL of 10 N sulfuric acid solution was added to stop the reaction. The absorbance of the glucose measurement reaction solution at a wavelength of 540 nm was measured. From the slope of a concentration standard curve made using varying concentrations of glucose solution, the concentration of glucose produced by the lactose degradation reaction of beta-galactosidase was calculated.

Next, in order to examine the substrate specificities of the wild-type and C-terminal deletion mutant beta-galactosidase proteins, according to the method described in Example 4, specific activities for two enzymatic substrates (lactose and oNPG) were measured and divided by the amount of the cells, thereby determining substrate specificities.

As shown in FIG. 5, the C-terminal deletion mutant beta-galactosidases, BgaII-873, BgaII-900, BgaII-950, BgaII-1000, BgaII-1059, BgaII-1066, BgaII-1115, BgaII-1064, BgaII-1200, BgaII-1302, and BgaII-1350, all showed higher values than the wild-type BgaII, suggesting that the C-terminal deletion mutants more easily use lactose than oNPG.

Example 6: Measurement of Galactooligosaccharide Synthesis Ability of Wild-Type and C-Terminal Deletion Mutant Beta-Galactosidase (BgaII) Proteins The wild-type and C-terminal deletion mutant beta-galactosidase proteins can synthesize galactooligosaccharide from lactose. 50% lactose solution in 100 mM potassium phosphate buffer was prepared, and 2 U of beta-galactosidase per g of lactose was added to the lactose solution, and a galactooligosaccharide synthesis reaction was performed at 50° C. for 24 hours. The reaction solution was treated with boiling water for 5 minutes to stop the enzymatic reaction. Carbohydrates in the sample were quantitatively analyzed using a Sephadex column (BioRad, USA) and HPLC (Agilent, Germany). 0.1% sulfuric acid solution was used as an elution buffer, and a refractometer was used to detect carbohydrates.

As shown in FIG. 6, the results of HPLC analysis of the wild-type beta-galactosidase (BgaII) and the C-terminal deletion mutant beta-galactosidase (BgaII-950) having a deletion mutation after amino acid residue 950 indicated that BgaII-950 produced an increased amount of glucose for the same time, compared to the wild-type beta-galactosidase, and indicated that BgaII-950 produced an increased amount of a galactooligosaccharide (GOS5) consisting of five hexose units, compared to the wild-type beta-galactosidase.

Example 7: Measurement of Thermal Stabilities of Wild-Type and C-Terminal Deletion Mutant Beta-Galactosidase (BgaII) Proteins The galactooligosaccharide synthesis reaction of beta-galactosidase (BgaII) occurs at a relatively high temperature of 50° C. Thus, the thermal stability of the enzyme is an important characteristic in the industrial application of the enzyme. In order to examine the thermal stabilities of the wild-type and C-terminal deletion mutant beta-galactosidase (BgaII) proteins, BgaII, BgaII-873, BgaII-900, BgaII-950, BgaII-1000, BgaII-1059, BgaII-1066, BgaII-1115, BgaII-1064, BgaII-1200, BgaII-1302, and BgaII-1350, each of the proteins was heat-treated in a water bath at 60° C. for 1 hour, and the residual enzymatic activity of each protein was measured using oNPG as an enzymatic substrate. The residual enzymatic activity was expressed as the ratio of the enzymatic activity of heat-treated beta-galactosidase to the enzymatic activity of non-heat-treated beta-galactosidase.

As shown in FIG. 7, the wild-type beta-galactosidase lost 70% of its enzymatic activity due to 1 hour of heat treatment, whereas the C-terminal deletion mutant beta-galactosidase (BgaII) proteins, BgaII-873, BgaII-900, BgaII-950, BgaII-1000, BgaII-1059, BgaII-1066, BgaII-1115, BgaII-1064, BgaII-1200, BgaII-1302, and BgaII-1350 retained 60% or more of their enzymatic activity, indicating that the thermal stabilities of the C-terminal deletion mutant beta-galactosidase (BgaII) proteins were better than that of the wild-type beta-galactosidase.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

Using the beta-galactosidase mutant according to the present invention, galactooligosaccharide can be efficiently produced in large amounts.

The invention claimed is:

1. A beta-galactosidase mutant having improved thermal stability or enzymatic activity compared to a wild-type beta-galactosidase set forth in the amino acid sequence of SEQ ID NO: 3 by deleting C-terminus of a beta-galactosidase set forth in the amino acid sequence of SEQ ID NO: 3, wherein the deletion of C-terminus is one or more selected from the group consisting of:

a) a C-terminal deletion mutation after amino acid residue 799;

b) a C-terminal deletion mutation after amino acid residue 873;

c) a C-terminal deletion mutation after amino acid residue 950;

d) a C-terminal deletion mutation after amino acid residue 1000;

e) a C-terminal deletion mutation after amino acid residue 1059;

f) a C-terminal deletion mutation after amino acid residue 1066;

g) a C-terminal deletion mutation after amino acid residue 1115;
h) a C-terminal deletion mutation after amino acid residue 1164;
i) a C-terminal deletion mutation after amino acid residue 1302; and
j) a C-terminal deletion mutation after amino acid residue 1350.

2. The beta-galactosidase mutant of claim 1, wherein the amino acid sequence of the mutant is SEQ ID NOs: 4, 6, 10, 12, 14, 16, 18, 20, 24 or 26.

3. A gene encoding a beta-galactosidase mutant of claim 1.

4. A recombinant microorganism into which the gene of claim 3 or a recombinant vector comprising the gene of claim 3 is introduced.

5. The recombinant microorganism of claim 4, wherein said microorganism is *Bacillus subtillis*.

6. A method for producing a beta-galactosidase mutant, comprising the steps of:
   expressing the beta-galactosidase mutant by culturing the recombinant microorganism of claim 4; and
   recovering the expressed beta-galactosidase mutant.

7. A method for producing a galactooligosaccharide, comprising:
   reacting a lactose-containing substrate with a beta-galactosidase mutant of claim 1 to produce galactooligosaccharide; and
   recovering the produced galactooligosaccharide.

* * * * *